United States Patent
Wang et al.

(10) Patent No.: US 7,235,045 B2
(45) Date of Patent: Jun. 26, 2007

(54) FLUORESCENCE IMAGING ENDOSCOPE

(75) Inventors: Thomas D. Wang, Mountain View, CA (US); Michael S. Feld, Newton, MA (US); Yang Wang, Blue Bell, PA (US); Jacques Van Dam, San Carlos, CA (US); Stephen F. Fulghum, Marblehead, MA (US)

(73) Assignees: Massachusetts Institute of Technology, Cambridge, MA (US); The Brigham and Women's Hospital, Inc., Boston, MA (US)

( * ) Notice: Subject to any disclaimer, the term of this patent is extended or adjusted under 35 U.S.C. 154(b) by 0 days.

(21) Appl. No.: 10/393,028

(22) Filed: Mar. 20, 2003

(65) Prior Publication Data
US 2003/0191368 A1 Oct. 9, 2003

Related U.S. Application Data

(63) Continuation of application No. 09/238,664, filed on Jan. 26, 1999, now Pat. No. 6,537,211.

(60) Provisional application No. 60/072,455, filed on Jan. 26, 1998.

(51) Int. Cl.
*A61B 1/04* (2006.01)
*A61B 1/06* (2006.01)

(52) U.S. Cl. ............... 600/109; 600/178; 600/477; 600/478

(58) Field of Classification Search ............ 600/109, 600/178, 160, 476, 478; 250/461.2, 372, 250/373
See application file for complete search history.

(56) References Cited

U.S. PATENT DOCUMENTS

| 4,253,447 A | 3/1981 | Moore et al. ............ 128/6 |
| 4,261,344 A | 4/1981 | Moore et al. ............ 128/6 |
| 4,604,992 A | 8/1986 | Sato ...................... 128/6 |
| 4,746,203 A | 5/1988 | Nishioka et al. ........ 350/401 |

(Continued)

FOREIGN PATENT DOCUMENTS

DE 195 35 114 A1 3/1996

(Continued)

OTHER PUBLICATIONS

"IV6C5-20/35", *Olympus Industrial Endoscope Products*, pp. 1-2, downloaded Apr. 24, 1996 from http://www.infoweb.... e/iv6c5-20_30E.html.

(Continued)

*Primary Examiner*—John P Leubecker
(74) *Attorney, Agent, or Firm*—Weingarten, Schurgin, Gagnebin & Lebovici LLP

(57) ABSTRACT

An endoscope having an optical guide that is optically coupled to a first broadband light source and a second laser light source that emits light at a wavelength in a range of 350 nm to 420 nm. The endoscope has an image sensor at a distal end and collects a reflectance image including red, green and blue components with the image sensor in response to illumination by said broadband light source. The image sensor also collects an autofluorescence image having a blue component, a green component and a red component. A processor processes the fluorescence image by determining a ratio of the fluorescence image and the reflectance image to provide a processed fluorescence image.

32 Claims, 12 Drawing Sheets

U.S. PATENT DOCUMENTS

| | | | | |
|---|---|---|---|---|
| 4,821,117 A | * | 4/1989 | Sekiguchi | 348/68 |
| 4,846,155 A | | 7/1989 | Kimura | 128/6 |
| 4,860,095 A | | 8/1989 | Kimura et al. | 358/98 |
| 4,957,114 A | * | 9/1990 | Zeng et al. | 600/476 |
| 4,981,138 A | * | 1/1991 | Deckelbaum et al. | 600/477 |
| 5,001,556 A | * | 3/1991 | Nakamura et al. | 348/70 |
| 5,058,568 A | | 10/1991 | Irion et al. | 128/4 |
| 5,187,572 A | | 2/1993 | Nakamura et al. | 358/98 |
| 5,228,430 A | | 7/1993 | Sakamoto | 128/6 |
| 5,255,087 A | * | 10/1993 | Nakamura et al. | 348/71 |
| 5,305,098 A | | 4/1994 | Matsunaka et al. | 348/65 |
| 5,363,854 A | * | 11/1994 | Martens et al. | 600/477 |
| 5,381,784 A | | 1/1995 | Adair | 128/6 |
| 5,396,329 A | | 3/1995 | Kalawsky | 356/364 |
| 5,421,339 A | | 6/1995 | Ramanujam et al. | 128/665 |
| 5,438,975 A | | 8/1995 | Miyagi et al. | 600/109 |
| 5,452,723 A | | 9/1995 | Wu et al. | 128/664 |
| 5,494,483 A | | 2/1996 | Adair | 600/111 |
| 5,701,903 A | | 12/1997 | Sano et al. | 128/665 |
| 5,719,399 A | | 2/1998 | Alfano et al. | 250/341.3 |
| 5,749,830 A | * | 5/1998 | Kaneko et al. | 600/160 |
| 5,769,792 A | * | 6/1998 | Palcic et al. | 600/477 |
| 5,772,580 A | | 6/1998 | Utsui et al. | 600/160 |
| 5,793,886 A | | 8/1998 | Cok | 382/169 |
| 5,827,190 A | * | 10/1998 | Palcic et al. | 600/476 |
| 5,840,017 A | | 11/1998 | Furusawa et al. | 600/160 |
| 5,847,394 A | | 12/1998 | Alfano et al. | 250/341.8 |
| 5,865,754 A | | 2/1999 | Sevick-Muraca et al. | 600/476 |
| 5,891,016 A | | 4/1999 | Utsui et al. | 600/181 |
| 5,999,844 A | * | 12/1999 | Gombrich et al. | 600/476 |
| 6,061,591 A | | 5/2000 | Freitag et al. | 600/476 |
| 6,124,597 A | | 9/2000 | Shehada et al. | 250/461.2 |
| 6,161,031 A | | 12/2000 | Hochman et al. | 600/407 |
| 6,201,989 B1 | | 3/2001 | Whitehead et al. | 600/476 |
| 6,296,608 B1 | * | 10/2001 | Daniels et al. | 600/104 |
| 6,422,994 B1 | | 7/2002 | Kaneko et al. | 600/160 |
| 6,790,174 B2 | | 9/2004 | Kaneko et al. | 600/118 |

FOREIGN PATENT DOCUMENTS

| | | |
|---|---|---|
| WO | WO 89/02718 | 4/1989 |
| WO | WO 92/15008 | 9/1992 |
| WO | WO 92/19148 | 11/1992 |
| WO | WO 93/25137 | 12/1993 |
| WO | WO 94/09694 | 5/1994 |
| WO | WO 94/23539 | 10/1994 |
| WO | WO 95/11624 | 5/1995 |
| WO | WO 95/26674 | 10/1995 |

OTHER PUBLICATIONS

"IK-SM40 Super Micro Camera", *Toshiba Review* (f02index. htm'95.11.1), total of 4 pages, downloaded Apr. 24, 1996 from http://www.toshiba....95/11/f02/index.htm.

Perelman, L.T., et al., "Spectroscopic diagnostics of epithelial tissues with polarized light". (From SPIE Abstract) No date given.

Wang, T., et al., "Model of Endoscopic Image Formation with Application to Fluorescence of Biological Tissue", pp. 1-33 (1998).

Tappy, T., et al., "Systeme d'entrainement pour chirugie endoscopique utilisant la realite virtuelle", pp. 1-5 No date given.

Wang, T., et al., "Laser-induced fluorescence endoscopic imaging for detection of colonic dysplasia". Presented at SPIE Meeting. (Feb. 4, 1995).

Wang, T., et al., "Real-time in vivo endoscopic imaging of fluorescence from human colonic adenomas". Paper presented at the meeting of the Society of Photonics Instrumentation Engineering—Systems and Technologies for Clinical Diagnostics and Drug Discovery, San Jose, CA (Jan. 1998).

Wang, T., et al., "Fluorescence Endoscopic Imaging of Human Colonic Adenomas", *Gastroenterology*, pp. 1182-1191 (Nov. 1996).

Wang, T., et al., "In Vivo Identification of Colonic Dysplasia Using Fluorescence Endoscopic Imaging", pp. 1-38 (Jun. 10, 1998).

Zonios, G., et al., "Diffuse Reflectance Spectoscopy of Human Adenomatous Colon Polyps In Vivo", pp. 1-30 (1998).

Wang, T., "Fluorescence Endoscopic Imaging System for Detection of Colonic Adenomas", pp. 5-192 (1996).

Wang, T., et al., "Mathematical Model of Fluorescence Endoscopic Image Formation", pp. 1-38 (1998).

\* cited by examiner

FLUORESCENCE IMAGING ENDOSCOPE

CROSS REFERENCES TO RELATED APPLICATIONS

This application is a continuation application of U.S. patent application Ser. No. 09/238,664, filed Jan. 26, 1999, now U.S. Pat. No. 6,537,211, which claims the benefit of U.S. Provisional Application No. 60/072,455 filed on Jan. 26, 1998, the entire contents of which is incorporated herein by reference.

GOVERNMENT SUPPORT

The invention was supported, in whole or in part, by grant numbers CA53717, P41RR02954, and DK 39512 from National Institutes for Health. The Government has certain rights in the invention.

BACKGROUND OF THE INVENTION

The following relates to the development of a laser-induced fluorescence imaging endoscope for mapping cancerous or precancerous tissues in hollow organs. In initial clinical studies, on colon polyps, Ultraviolet (UV) light was used at 370 nm to excite visible fluorescence (400-700 nm), the spectral signatures of which enabled differentiating between normal and abnormal tissues. Previously endoscopic imaging has been achieved using an optics module mounted in one of the biopsy ports of a two-port standard (white light) colonoscope. The optics module employs a quartz optical fiber and associated optics to deliver the UV light to the tissue, and a coherent quartz fiber-optic bundle to transmit the resulting fluorescence image to the proximal side of the endoscope, where a filter removes the large background of reflected UV light and the fluorescence image is then captured by a high-gain CID detector array.

Endoscopically-collected autofluorescence images of colonic mucosa can be used as a screening tool for detecting pre-cursors to colorectal cancer (CRC). Fluorescence has been used to distinguish between normal mucosa and adenomas. In particular, spectra measured with single point contact probes with the use of several different excitation wavelengths.

Fluorescence spectra have been obtained through optical fiber probes with several excitation wavelengths. An in vitro study performed a search over a wide range of excitation wavelengths, and concluded that 370 nm is optimal for distinguishing between normal mucosa and adenoma. Both in vitro and in vivo studies using adenomatous polyps as a model for dysplasia have shown that with this wavelength dysplasia has less peak intensity at 460 nm and may have increased fluorescence at 680 nm compared with normal colonic mucosa. Furthermore, the morphologic basis for these spectral differences has been studied by fluorescence microscopy. The decreased fluorescence intensity in polyps was attributed to its raised architecture, increased vasculature, and reduced collagen in the lamina propria. The red enhancements arise from increased fluorescence of the crypt cells, which may be caused by higher levels of porphyrin.

SUMMARY OF THE INVENTION

The present invention relates to imaging endoscopes and in particular to a fluorescence imaging colonoscope using a dual channel electronic endoscope that employs a charge coupled device (CCD) chip or other solid state imaging device mounted on its distal tip to collect the white light image. Of particular significance for the present invention is that this chip can also collect the fluorescence image, displaying it on the endoscope's video monitor with much larger signal size than that obtained using the optics module and intensified CID camera. This configuration was used to collect fluorescence images of colonic dysplasia. Video images of two small FAP polyps, have been taken with the standard white light image and the unprocessed fluorescence image.

The CCD detector, which lacks gain intensification, detects the weak fluorescence signals, which are six orders of magnitude smaller in intensity than the diffusely reflected white light image. In addition, it is surprising that reflected 370 nm excitation light did not completely flood the CCD, obscuring the fluorescence signal. This results from the fact that the CCD spectral response falls off to zero quickly at wavelengths below 400 nm. Thus, the CCD effectively serves as its own long pass filter. Other imaging devices can be used with a filter to reduce by at least one half the detected intensity in the ultraviolet region relative to the detected intensity in the visible region.

In this particular embodiment, the CCD has a resolution of 270×328 pixels and an objective lens of 2.5 mm in diameter. The images are collected in 33 ms in RGB format. The advantages of this particular embodiment include that the in vitro fluorescence images exhibit a signal-to-noise ratio (SNR) of about 34 at clinical working distances of 20 mm (distance between tip of endoscope and tissue surface), which is superior to that obtained using the UV Module/CID detector, which has a SNR of about 18 at the same distance. The use of the CCD eliminates the need for the optics module and greatly simplifies system design. In addition, it also avoids problems associated with the tendency of the UV module to rotate in the biopsy channel. By using the same detector and optics for white light and fluorescence images, perfect registration of these two images can be obtained. Parallax between the white light image of the CCD and the fluorescence image of the optics module was a significant problem. The CCD in this particular embodiment contains 88,560 pixels compared to 10,000 fibers for the UV module, resulting in higher total image resolution. The objective lens on the Pentax colonoscope has better imaging properties than the UV module. The characteristic width for the line spread function of the lens of this embodiment is 200 mm compared to 400 mm for the UV Module. The overall rigidity of the spectral endoscope is not increased significantly with a single UV illumination fiber.

The diagnostic methods employed can be based on the overall fluorescence intensity difference between normal mucosa and dysplasia. Thus, in certain applications it is preferable to collect the fluorescence emission over the full band between 400-700 nm. However, accurate measurements can use a point contact device such that diagnostic information can be obtained by sampling the fluorescence at a plurality of specific wavelengths such as 460, 600 and 680 nm, for example. For many applications the preferred range for fluorescence excitation is between 350 nm and 420 nm. Endoscopic imaging studies with the electronic CCD endoscope can include the use of color CCD's, which have the ability to provide such information.

DETAILED DESCRIPTION OF THE INVENTION

The equations describing the number of signal photons, $N_s$, collected by a given pixel in an endoscope as a function of the separation distance d and the radial distance $\rho$ on the tissue surface, and the corresponding SNR are as follows:

$$N_s(p) = \frac{\eta_s \lambda_{em} g^2 T_f T_i T_o f_p r_L^2 \varepsilon_t(\lambda_{em}, \Delta\lambda) \tan\theta_m^2 P_o(\lambda_{ex}) \Delta t}{hc \; 8(1-\cos\theta_m) N_f d^2 \left(1 + \left(\frac{p}{d}\right)^2\right)^{3.5}} \quad (1)$$

$$SNR = \frac{N_s}{\sqrt{N_s + \left(\frac{\sigma_e}{G}\right)^2}}$$

Figure 1:
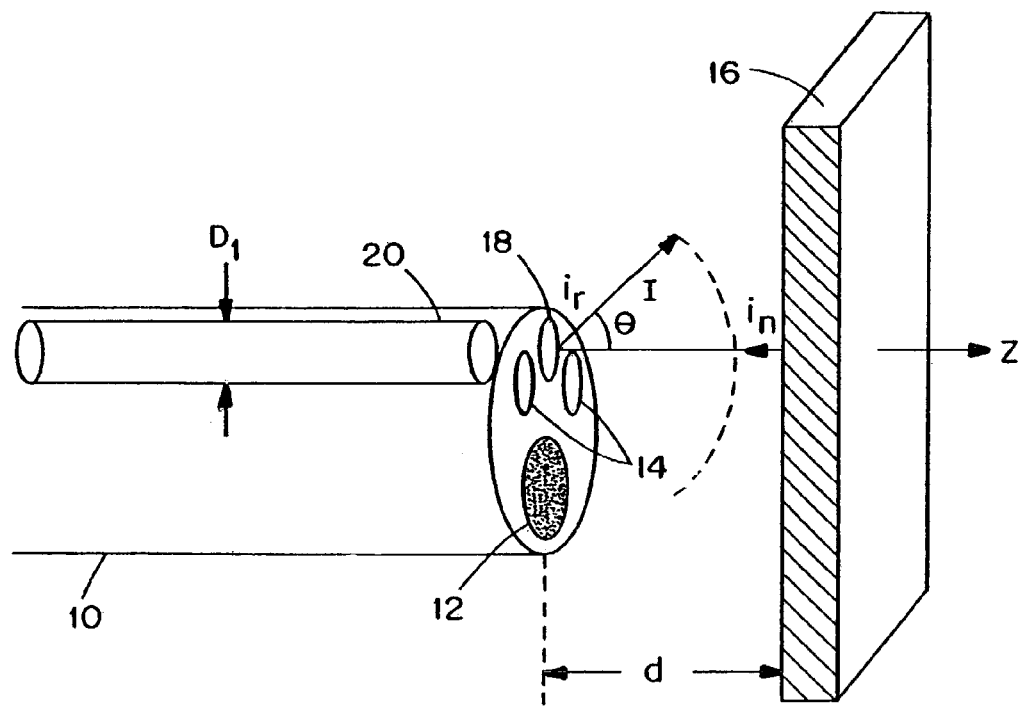
FIG. 1 is a schematic view of an endoscopic system.

The geometry and certain symbols are defined in FIG. 1. Note also the emission wavelength $\lambda_{em}$, pixel array size g×g, fiber optic transmission efficiency $T_i$, the bandwidth of the filtered emission wavelength $\Delta\lambda$, the fraction of the transmitted energy in this wavelength region $T_f$, the collective efficiency $T_o$ of the system optics including the long pass filter, lens and eyepiece, incident light energy $P_o(\lambda_{ex})\Delta t$,h is Planck's constant, c is the speed of light, $f_p$ is the packing fraction of the fiber cores $\varepsilon_t$ is the quantum efficiency of the tissue, and $N_f$ is the total number of resolution elements. The signal to noise ratio (SNR) is a function of electronic noise $\sigma_e$ and gain G.

Colorectal cancer constitutes a major national health care problem. The incidence and mortality for carcinomas of the colon and rectum are second only to those of lung in the United States. This suggests that the current screening methods are inadequate for controlling the spread of colon cancer, and that little advancement in detection has occurred in a long time. The five year survival rate for all patients diagnosed is between 35-49%. Colorectal cancer is relatively unresponsive to radiation and chemotherapy, hence surgical resection with wide margins is the only reliable method of preventing its growth. These tumors spread by direct extension into adjacent structures and by metastasis through the lymphatics and blood vessels. The most common sites of metastatic spread in order are regional lymph nodes, liver, lungs, and bones.

The pathophysiology of this disease begins in the epithelial layer of colonic mucosa as dysplastic changes in the crypts cells. This tissue can be accessed by colonoscope, and if the pre-malignant lesions are detected at an early stage, they can be removed for biopsy. Most carcinomas of the colon and rectum are believed to arise from visible precursor lesions called adenomatous polyps. These benign masses evolve from a monoclonal expansion of epithelial cells which develop irregularities in the size and shape of the nuclei and cytoplasm, a condition known as dysplasia. These lesions can be detected on colonoscopy by their raised architecture. The medically accepted adenoma-carcinoma sequence suggests that colorectal carcinoma arises from adenomatous tissue that undergoes malignant transformation, which is believed to occur through a multistep process in which genetic alterations accumulate. The presence of a precursor stage in the development of CRC provides a window of opportunity for early detection and removal of these lesions to prevent future progression into carcinoma.

The prevalent screening method of colonoscopy relies on the observation of large structural changes in the colonic mucosa in order to locate adenomatous tissue for biopsy. However, this procedure is relatively insensitive to adenomatous tissue which is flat. Patients diagnosed with ulcerative colitis (UC), for example, have a high risk of developing carcinoma from non-polypoid regions of tissue. Moreover recent studies have concluded that some forms of adenocarcinoma arise from small superficial adenomas. Because of this risk, frequent screening by colonoscopy must be performed with multiple biopsies throughout the colon. However, the likelihood of sampling error and missed diagnoses in these patients renders this form of surveillance highly unsatisfactory. Also, the examination of a tissue biopsy is time consuming and costly. Moreover, considerable intra- and inter-observer variation occurs in the identification of dysplasia. A patient who is diagnosed as positive for dysplasia often must return to the clinic for further screening and possibly for surgical resection of the colon. Thus, the current state of endoscopic surveillance with histologic interpretation is an imperfect science and is in need of improved methodologies with greater sensitivity and specificity and less intra- and inter-observer variation.

The method of fluorescence endoscopic imaging offers features which can overcome the present screening limitations with white light endoscopy. This method is sensitive to the biochemical constituents and microarchitecture below the tissue surface. Furthermore, combined with endoscopes, fluorescence images can scan wide areas, and can resolve tissue surfaces on the sub-millimeter scale. If sufficient information is present on the fluorescence, computers can be used to determine the presence and location of diseased regions in real-time. Autofluorescence has demonstrated the ability to distinguish between normal and neoplastic human tissue. The first studies showed that single point fluorescence spectra can be used to detect tumors in vitro from several types of tissue. Later, in vivo studies were performed for detecting neoplasia in bladder, brain, colon, cervix, esophagus, lung, oral mucosa, and skin. In addition, fluorescence has been used to distinguish normal tissue from diseased with the use of exogenous agent such as hematoporphyrin derivative (HpD).

The full length from the rectum to the cecum is typically 1.5 m. Histologically, the mucosa is the layer in contact with the lumen, and has a thickness of about 400 µm. The epithelium is the most superficial layer and consists of absorptive columnar cells and intermittent mucin-producing goblet cells, which function to reabsorb water and to lubricate. These cells undergo continuous turnover, and are replaced by rapidly dividing stem cells at the base of the crypts, where the first signs of dysplasia can be observed. The surrounding lamina propria contains blood and lymphatic capillaries which supports the secretory, absorptive and other highly active functions of the mucosa. It consists of loose connective tissue, in particular collagen, along with numerous inflammatory cells which protect the intestinal wall from invasion by microbes.

The muscularis mucosa is composed of several layers of smooth muscle fibers which contract to expel secretions from the glandular crypts, prevents clogging, and enhances absorption by maintaining contact between epithelium and luminal contents. The submucosa contains the larger blood vessels, lymphatics, and nerves, and are surrounded by dense collagenous connective tissue which keeps the mucosa attached to the muscularis propria. The muscularis propria contains an inner circular and outer longitudinal muscle layer, which are involved in the involuntary peristaltic contractions of the colon for propagating the flow of fecal matter. The outer serosal layer consists of connective tissue which contain the major blood vessels and nerves.

Adenomatous polyps are raised protrusions of mucosa which contain immature, poorly differentiated epithelial cells with irregularity in size and shape of the nuclei. These lesions are benign but they have the potential to transform into colorectal carcinoma. The different morphological types include tubular, villous, and tubulovillous adenomas. Although all forms are raised, each type can either contain a stalk, which is called pedunculated, or can be hemispheric, which is known as sessile. The malignant potential of polyps are greatest with the villous form and least with the tubular. Also, the probability of carcinoma developing increases with the size of the polyp. There is about a 1% chance of finding invasive tumor in a polyp less than 1 cm in diameter, 10% for polyps between 1 and 2 cm, and 45% for polyps larger than 2 cm. The sub-cellular changes associated with these polyps are frequently histologically identical to the dysplasia found in ulcerative colitis.

Results of molecular biology studies suggest that the steps involved in the malignant transformation of adenoma into carcinoma involves the mutational activation of an oncogene coupled with the sequential loss of several tumor suppressor genes. Also, it was found that several genes must incur mutations before malignant tumors arise. Several specific genetic alterations have been identified during the process of tumorigenesis. Activational mutations have been found in the ras oncogene of 50% of colorectal carcinoma. Furthermore, allelic deletions were identified in portions of chromosomes 5, 17, and 18, which may involve loss of tumor-suppressor genes.

Patients with the presence of over 100 neoplastic polyps in their colon are diagnosed with the condition called familial adenomatous polyposis. These people have a genetic predisposition for developing numerous polyps in their colon by adulthood. Most patients have between 500 and 2500 polyps, and on average, there are about 100 polyps. FAP is a rare disease, and accounts for only about 1% of the incidence of CRC in the Western world. Foci of dysplasia usually become malignant, and FAP patients must have their colons removed at a young age. The probability for the onset of colon cancer for someone with this condition is 10% at 10 years of age, 50% at 20 years, and 100% at age 30. Histologically, most of the polyps are tubular adenomas with a high probability of malignant transformation, and the dysplasia associated with FAP polyps is identical to that found in sporadic polyps. An autosomal dominant genetic defect is responsible for the development of this disease.

A second form of CRC that is associated with familial predisposition is hereditary nonpolyposis colorectal cancer (HNPCC). HNPCC is defined as patients with at least three relatives in two generations having CRC, and with at least one relative being diagnosed at less than 50 years old. This form is much more common than FAP, and accounts for up to 13% of the incidences of CRC in the Western world. HNPCC patients do not have numerous adenomatous polyps, and it is very difficult to distinguish it from sporadic cases. Genetic linkage has been found between this disease and anonymous microsatellite markers on chromosome 2.

In ulcerative colitis, the mucosa undergoes cytological changes resulting in the formation of dysplasia without the presence of polyp formation. These changes are believed to be associated with repeated episodes of chronic inflammation and repair of the colonic epithelium, and flat, ulcerated tumors with poorly defined margins are common. Patients who have had UC for over 8 years are recommended to have periodic colonoscopy with random biopsies taken. This screening process is not effective because less than 0.1 percent of the total mucosal surface area is sampled. However, it is important to note that only 1% of new incidences of CRC arise from UC cases.

UC is an inflammatory disorder of the colorectal mucosa of unknown cause. Patients with UC are at increased risk for developing dysplasia or cancer. Recognition of this increased risk has resulted in colonoscopic surveillance strategies starting at 7-10 years after the initial presentation of symptoms. Colonic surveillance strategies include direct macroscopic visualization of colonic mucosa and access to mucosal biopsies for microscopic assessment of dysplasia. Although the pathological classification of dysplasia was standardized in 1983, differences and inconsistencies remain regarding the interpretation of dysplasia.

Dysplasia is typically focal. Despite the practice of taking 12-20 mucosal biopsies during surveillance colonoscopy, less than 1% of the colonic surface is sampled, so the likelihood of missing small foci of dysplasia is high. Thus, cancers can develop in patients without any previous or concurrent dysplasia. Although performing prophylactic colectomy on all patients after the first decade of disease would be the most definitive solution to the cancer problem in UC, patients with minimal or mild symptoms of the disease are understandably reluctant to take this radical approach. Colonoscopic surveillance with histologic interpretation remains an imperfect science in need of improved methodologies with greater sensitivity and specificity.

Furthermore, studies have suggested that flat dysplasia may be the origin of sporadic colon cancer which does not arise via the adenoma-carcinoma sequence. The morphological characteristics of adenomas that proliferate superficially in flat nonpolypoid mucosa have been observed endoscopically as small plaquelike lesions with vague redness or discoloration. In a comprehensive study, 33 such lesions were described as slightly elevated with a reddish surface and a central depression. Foci of cancer or severe atypia were found in 25% of lesions of diameter up to 4 mm, 40% of lesions measuring between 5 and 8 mm, and 80% of lesions with diameter between 9 and 10 mm.

There are several methods in practice for the early screening for CRC, but each is limited in its effectiveness. The goal of screening is to detect localized superficial masses in asymptomatic individuals.

A sigmoidoscopy involves the clinician viewing the patient's rectum and sigmoid colon with either a rigid or flexible imaging device. This form of screening is based on the finding that 60% of CRC occur within the distal 25 cm of the colon. This length is reachable with a rigid sigmoidscope, and a flexible one can reach up to 60 cm. However, recent statistics have shown that an increasing number of tumors are found beyond the reach of this device. An advantage of this procedure is that it can be performed without the patient undergoing anesthesia or taking a prep. The most extensive method of screening for this disease is a colonoscopy, where the patient is first prepped and sedated. A colonoscope is inserted throughout the full length of the colon, and the mucosal surface is viewed by the physician under white light for polyps and other abnormal masses. This procedure is adequate for identifying raised lesions, but flat region of dysplasia will go undetected.

The fluorescence of tissue occurs through a process in which the electrons of a biological molecule enters an elevated energy state upon absorbing laser light at a given excitation wavelength $\lambda_{ex}$. The excited state is unstable, and the electrons will return to the ground state. Most of this energy is lost as heat through molecular collisions, but a small fraction of excited electrons undergo an internal conversion and spontaneously radiates light at longer emission wavelengths $\lambda_{em}$. The fraction of molecules which release energy by fluorescence is called the quantum efficiency of the tissue, denoted as $\epsilon_t$. The fluorescence intensity depends on the product of the initial population of the excited state and the tissue quantum efficiency.

The spectral lineshape is determined by the fluorescence emission and absorption by biochemical molecules which are unique to the composition of tissue. The electronic levels of the single state are split into vibrational and rotational states, which in large molecules consists of small intervals and may overlap due to molecular interactions. The electrons may decay to any of the vibrational-rotational levels of the ground state; thus, the fluorescence spectra of biomolecules are typically broad. This lack of structure in the spectra limits the amount of information that can be obtained from fluorescence. The tissue components which produce fluorescence are known as fluorophores, and endogenous chromophores include aromatic amino acids, NADH, FAD, and porphyrins. The local environment may have a large effect on the fluorescence emission, which may become quenched or shifted in wavelength. Further details regarding the use of outafluorescence for imaging tissue can be found in U.S. Pat. Nos. 4,193,142, 5,421,337, 5,452,723, 5,280,788 and 5,345,941, the entire contents of these patents being incorporated herein by reference.

A first step taken in evaluating the use of fluorescence in colon was to determine the existence of optimal wavelengths to differentiate between normal colon mucosa and adenomatous polyps in vitro with single point measurements on a sub-millimeter scale. For example, the fluorescence emissions of 4 normal colon and 11 adenomatous polyps were recorded with a spectrofluorimeter. The excitation wavelengths used ranged between 250 to 500 nm in 10 nm steps, and the results were tabulated in an array called an excitation-emission matrix (EEM). A ratio was taken of the average EEM from the normal colon to that of the adenomatous polyps, and excitation at 330, 370 and 430 nm were found to produce fluorescence spectra which contained the greatest amount of diagnostic information.

Based on the results of these in vitro studies, clinical trials were conducted to evaluate the ability of fluorescence to distinguish among normal, adenomatous, and hyperplastic colon tissue with 370 nm. In this study, a pulsed nitrogen-pumped dye laser delivered 370 nm excitation through an optical fiber probe with one excitation and six collection fibers. This probe was inserted through the biopsy channel of a colonoscope, and placed in contact with the colonic mucosa during colonoscopy. The probe consisted of six individual 200 µm collection fibers arranged in a bundle with one fiber for excitation. With this device, fluorescence emission was detected from an area of tissue about 1 $mm^2$. The fluorescence spectra were detected by a spectrograph coupled to an OMA. The spectra showed a difference at 460 nm where the normal mucosa produced about 6 times greater fluorescence intensity than adenoma. This difference is almost twice that found from the in vitro studies. Above 650 mn, the average of the adenomas were slightly greater than that of normal.

From 20 patients, the fluorescence intensities at 466 and 680 nm were located on a scatter plot, and a straight line was drawn to minimize the number of misclassifications when compared to histology. The decision line correctly classified 31 of 31 adenomas, 3 of 4 hyperplastic polyps, and 31 of 32 normal colonic tissue specimens. The sensitivity, specificity and positive predictive value of the technique for diagnosing adenomas were 100%, 97%, and 94%, respectively. Because only a small number of hyperplastic polyps were examined, it was unclear whether adenoma could be reliably distinguished from hyperplasia using fluorescence. The observed differences in the fluorescence may arise from architectural differences between polyps and the normal mucosa rather than from dysplastic changes.

The next step was to use the data from this study to provide prospective methods of evaluating the performance of fluorescence. The data were randomly divided into two equal sets, and the first was used to devise an algorithm to distinguish the tissue type based on the fluorescence intensity at 460 nm and at the ratio between intensities at 680 to that at 600 nm. A biopsy of tissue from each point was classified histologically as adenomatous, hyperplastic, or normal. From the prospective decision criteria, the sensitivity, specificity and positive predictive value of the algorithm for diagnosing adenomas were 90%, 95%, and 90%, respectively.

Further attempts have been made to use fluorescence to distinguish between normal mucosa, adenomatous polyps and hyperplastic polyps in vivo with 337 nm excitation. Fluorescence spectra were measured from 86 normal colonic sites, 35 hyperplastic polyps, and 49 adenomatous polyps with a single optical fiber. The fluorescence emission displayed peaks at 390 and 460 nm, which was attributed to the collagen in the submucosa. Also, this peak decreased in intensity for normal mucosa, hyperplastic polyps, and adenomas, respectively. The peak intensity of the normal mucosa was found to be slightly less than twice that for adenomas. Using a MVLR analysis, the sensitivity, specificity, positive predictive value and negative predictive value of fluorescence to distinguish between adenomatous and hyperplastic polyps were 86%, 77%, 86% and 77%, respectively. This study concluded that the differences in fluorescence were due to polyp morphology rather than to the fluorophores present in the polyps.

Other excitation wavelengths have been used to study fluorescence in colon. A continuous wave He—Cd laser was used to deliver 325 nm excitation to measure fluorescence spectra from 35 normal mucosa and 35 adenomatous polyps in vitro from a single optical fiber by an OMA. The peak intensity from normal mucosa occurred at 375 nm and that for adenoma appeared at 450 nm. A multi-variate linear regression (MVLR) analysis established a set of scores for each data point to determine a diagnostic criterion. Fluorescence spectra from an additional 34 normal, 16 adenomatous, and 16 hyperplastic sites were taken and analyzed prospectively using the established decision criteria. The sensitivity, specificity and positive predictive value of this study to distinguish between normal and adenomatous tissue were found to be 100%, 100%, and 94%, respectively. In addition, 15 of 16 hyperplastic polyps were classified as normal, which is the correct diagnosis because hyperplastic polyps are formed from a thickening of the epithelial layer.

The fluorescence of colon was studied with 410 nm excitation as well. The emission from 450-800 nm was collected with a spectrofluorimeter from 83 biopsy specimens removed during colonoscopy from 45 patients. The intensity of the emission band from 460-530 nm declined from normal to carcinoma to adenomatous mucosa. The peak intensity at 460 nm was about 2.5 times higher for normal mucosa than for adenoma. A stepwise discriminant analysis was performed on the spectra using nine variables. The results compared to histology showed that the process distinguished between normal mucosa and adenoma with a sensitivity and specificity of 88.2% and 95.2%, respectively. The fluorescence emission resulted from the superposition of three bands centered at about 470, 485, and 404 nm.

Thus, there has been extensive research performed within the last 5 to 10 years to evaluate the use of tissue autofluorescence to distinguish between adenomatous and normal mucosa. In vitro studies have concluded that 330, 370, and 430 nm are optimal for excitation. Preliminary in vivo results indicate that single point fluorescence detection has a sensitivity, specificity, and positive predictive value as high as 90%, 95% and 90%, respectively for such discrimination. Also, the data suggest that the intrinsic fluorophores can include collagen, NADH, and porphyrin. Hemoglobin is an absorbing chromophore. In order to make this technique suitable for a clinical setting, wide area fluorescence detection and processing must be performed in real time and adapted to conventional white light endoscopy. These requirements demand the development of a spectral imaging instrument.

Fluorescence microphotographs of unstained frozen sections were studied to account for the morphological structures in normal colonic mucosa and adenomatous polyps which emit fluorescence. The 351 and 364 nm lines from an argon-ion laser were used for fluorescence excitation, and the emission was collected by a series of barrier filters with cut-off wavelengths of 420, 475, 515, 570 and 610 nm. The fluorescence intensity was graded semi-quantitatively from 1+ to 4+ by a single observer. In normal mucosa, fluorescence in the spectral band from 420 to 700 from collagen in the lamina propria was graded at 3+ and that in the submucosa at 4+in the same emission bandwidth. In the epithelium, there was faint fluorescence seen from absorptive cells and none from goblet cells. The H&E stained section identifies the tissue composition of normal mucosa. The fluorescence image of the serial unstained section indicated the fluorescent structures. Several differences were observed on the fluorescence image of the serial unstained section indicating the fluorescent structures.

Several differences were observed on the fluorescence micrographs of the adenomatous mucosa. First, fewer collagen fibers were present in the lamina propria, resulting in less fluorescence intensity from the epithelium. Also, the level of fluorescence seen in the cytoplasm of crypt cells was recorded at 2+, compared to +/− seen in normal crypts. Finally, a larger number of fluorescent granules were present in adenoma. The image of the H&E stained section include crypt cells from an adenomatous polyp. The fluorescence from the serial unstained section shows an observable level of fluorescence, and the number of eosinophils in the lamina propria is significantly larger than that in normal mucosa. The submucosa of the adenomatous polyp was graded at 4+, which is the same as that of normal.

A procedure has been developed to describe the clinically observed fluorescence in terms of its microscopic origins. This process combined the intrinsic fluorescence of each microstructure with its density as a function of tissue depth and the optical turbidity of the incident and return path. The concentrations of each fluorophore from clinical fluorescence spectra can then be extracted. From this procedure, the factors for observing greater fluorescence intensity from normal mucosa compared to that from adenomas include: (1) The submucosal fluorescence is about 10 times brighter than that of the overlying mucosa. (2) The mucosa attenuates both the incoming excitation light and the returning fluorescence; if the mucosa is sufficiently thick, the underlying submucosa cannot contribute, but if it is thin, as in normal mucosa, attenuation is smaller, resulting in brighter tissue fluorescence. (3) In addition, the fluorescence intensity of adenomas is less than that of normal colonic mucosa, perhaps because the dysplastic crypts tend to displace the collagen in the lamina propria, which is the dominant fluorophore. (4) Adenomas exhibit greater attenuation of both the 370 nm excitation light and the return fluorescence, due to increased hemoglobin-rich microvasculature.

Figure 2:
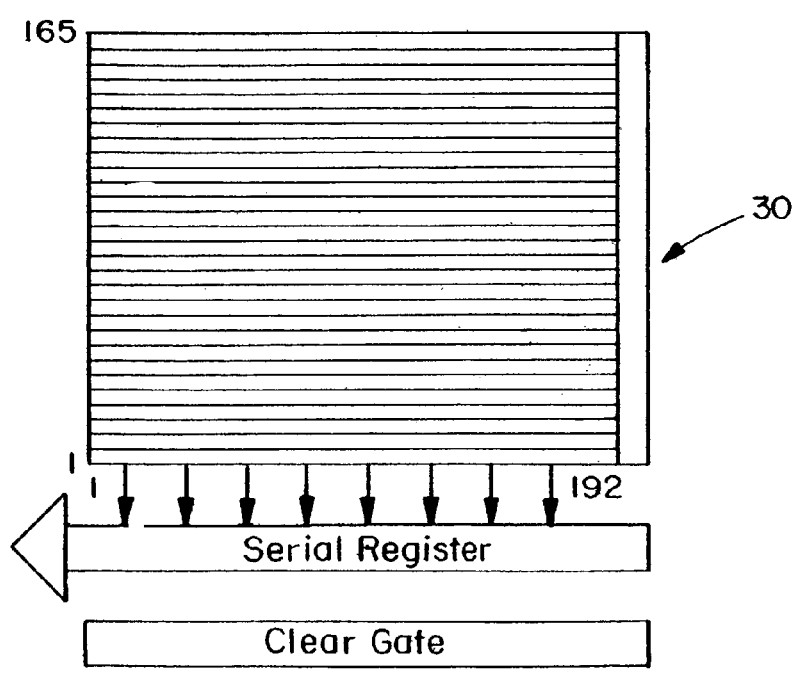
FIG. 2 is a schematic view of a solid state imaging device such as a CCD on the distal end of an endoscope.

A multi-spectral imaging system has been developed which collects fluorescence at four different emission wavelengths simultaneously. In this device, the output of a fiber optic endoscope is passed through 4 spatially separated interference filters. The 4 images are arranged onto quadrants of an intensified CCD array by adjustable segments of a multi-mirror system. The CCD or other imaging device 40 as seen in FIG. 2 can have 30,000 pixel elements or more. The four wavelengths were selected to optimize the contrast in the fluorescence spectra between normal and diseased tissue. Fluorescence from human cadaveric aorta was excited with 337 nm, and emissions from 400, 420, 450, and 480 nm were ratioed to produce a dimensionless contrast function. This function indicated a value for atherosclerotic plaque that was four times greater than that for normal artery, and the results were displayed using a false-color overlay. This instrument was also able to distinguish between rat tumor and surrounding muscle from fluorescence spectra. Further details regarding this system are described in Wang, T. D. et. al., "Real-time In vivo Endoscopic Imaging of Fluorescence from Human Colonic Adenomas", proceeding of SPIE 1998, 3259, the entire contents of which is incorporated herein by reference.

The resolution of this design is limited by the fibers in the imaging bundle. The use of 4 fluorescence emission wavelengths provides for greater contrast between normal and diseased tissue and for flexibility in the development of the disease detection process. However, by separating the fluorescence emission in parallel, the signal is reduced by a factor of 4, thus lowering the SNR. Also, the 4 spectral images must be aligned onto the detector at different angles, which poses a challenge for image registration. Furthermore, image processing algorithms using multiple images increase the computation time, and it is not clear that the fluorescence contains independent information at 4 bands. Finally, the fluorescence images are detected at the proximal end of the endoscope, which poses difficulty in clinical use for registering the white light image and in navigating the instrument.

A simpler version of the multi-spectral imaging system has been developed which collects only 2 emission bands. This design splits the fluorescence emission with a beam splitter onto two intensified CCD cameras. A helium cadmium laser delivers excitation light at 442 nm via the illumination bundle of a fiberoptic bronchoscope. The fluorescence emission was filtered in 2 bands, one between 480 and 520 nm and the other at wavelengths greater than 630 nm. The two spectral images were aligned, and the intensities were ratioed point by point for discriminating normal from diseased tissue, and a color image was formed. This method eliminates the effects of distance and angle of the illuminating light, as well as tissue reflective properties. A color camera is attached separately for observing the white light image. This system was tested clinically on 53 patients and 41 volunteers, and the results were compared with conventional white light bronchoscopy at 328 sites. The sensitivity on fluorescence was 73%, which was significantly greater than that of 48% found on white light in detecting dysplasia and carcinoma in situ. The two methods were found to have the same specificity of 94%.

In the clinical system, the white light and fluorescence images were collected with a dual-channel electronic colonoscope (Pentax EC-3800TL). This model contains two biopsy channels with diameters of 3.8 and 2.8 mm, respectively. The outer diameter of the endoscope is 12.8 mm, and the working length in 1.7 m. The field of view of the multi-element objective lens has a divergence half-angle of 60° with a depth of focus ranging between 5 and 100 mm. The white light illumination is produced by a 300 W short-arc xenon lamp. By using the same detector for both white light and fluorescence imaging, perfect registration can be obtained. This feature is ideal for producing a diagnostic overlay.

An illumination probe consisted of 200 μm core diameter optical fiber with NA=0.40 coupled to a 3 mm diameter BK7 glass microlens (F#=–1). The illumination probe was inserted into one of the instrument channels, and the tip was placed flush with the distal end of the colonoscope. A mode mixer clamped the excitation fiber at the proximal end to maximize the divergence angle of the light. The probe was attached at the proximal end of the colonoscope by a leur lock to prevent movement. A power of 300 mW was delivered to the tissue. The spectral response of the CCD detector (TI TC210) cuts off at about 400 nm, and is negligible at the excitation wavelengths $\lambda_{ex}$=351 and 364 $nm^3$, thus eliminating the need for a long pass filter to block specular reflection from the excitation light. The two instrument channels allow for the optical fiber illumination probe and the bioposy forceps to be used at the same time. FIG. 1 shows a schematic view of the endoscope 10 with an imaging bundle 20, bioposy view of the endoscope 10 with an imaging bundle 20, biopsy channel 12, lens 18, and illumination ports 14. The distal end of the device is positioned at a distance d from the tissue. One problem associated with such a system is the shadows generated by the illumination system. An important feature of the invention described below is a process to compensate for shadows on the tissue 16 surface.

Figure 3:
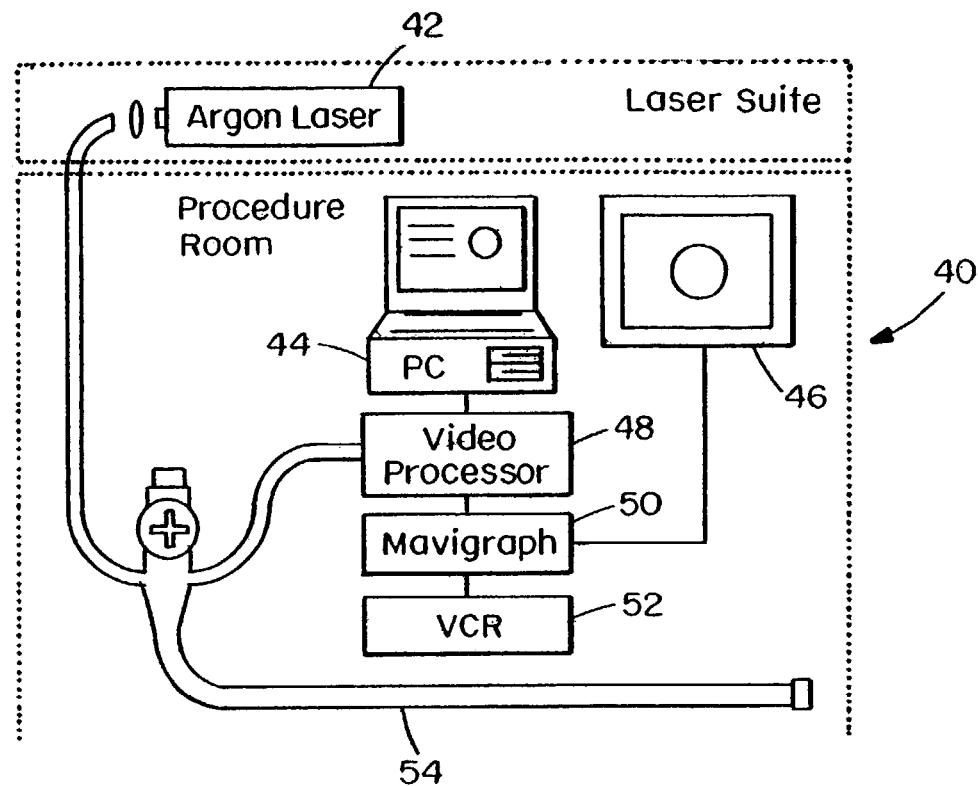
FIG. 3 is a schematic diagram of an endoscopic system in accordance with the invention.

A footswitch was activated by the user to block the excitation light when the white light was used for illumination, and vice versa, using a pair of computer controlled shutters (Uniblitz, VS14). The integration time for acquiring each fluorescence image is 33 ms. As shown in FIG. 3, the clinical fluorescence imaging system 40 consists of a video processor 48, computer 44, monitor 46, mavigraph 50, and VCR 52, laser 42 and colonoscope 54.

An electronic colonoscope 54 detects photons at the distal end with a CCD detector. An important aspect of the present invention is that the spectral response of the Texas Instrument TC-210 CCD detector dropped sufficiently fast below 400 nm that no diffuse reflection from the UV excitation was observed. In fact, virtually no specular reflection, which is several orders of magnitude higher in intensity than diffuse reflectance and fluorescence, was observed either. Another aspect which made this system possible was that the detector has sufficient sensitivity to detect fluorescence from colonic mucosa without the use of an intensifier. Because the detector is located at the distal end, the optical transmission efficiency is determined only by the multi-element objective lens positioned between the detector and the tissue. Another significant feature of this embodiment of the invention is that the same chip detects both the white light and fluorescence image, thus perfect registration occurs on the pseudo-color overlay. Furthermore, no modifications are necessary to the colonoscope which can impede the clinician's ability to perform the procedure.

One limitation of this system is the bandwidth selectivity and spectral resolution of the chip. The TC 210 is a monochrome detector and collects fluorescence over the full visible spectrum. It is difficult to employ bandpass filters in front of the CCD because the light is collected at angles at high as 60°. However, RGB detectors exist which contain pixels which are sensitive to red, green, and blue light, and can produce fluorescence images in 3 frames. However the passbands are determined by the integrated circuit manufacturer of the imaging circuit. Note that a gating mechanism can also be used, which is desirable for using pulsed lasers as the excitation source. Other excitation sources can include CW lasers and broad or narrow band light sources.

Figure 5:
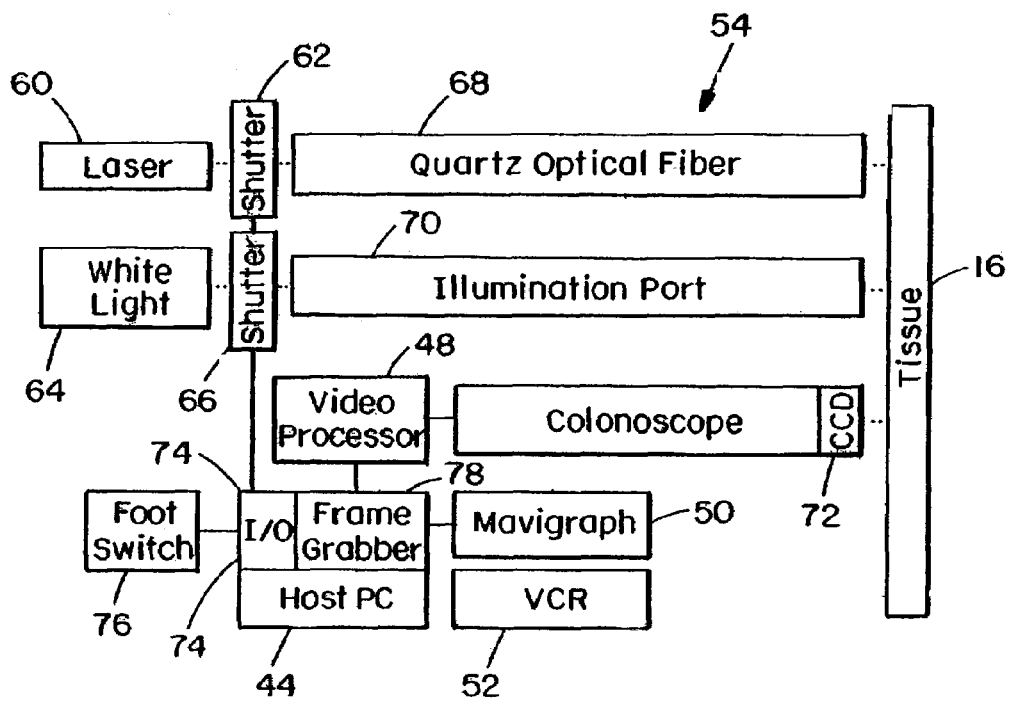
FIG. 5 is a schematic diagram of an endoscopic system.

The block diagram of an electronic imaging system operated by switch 76 is shown in FIG. 5. An argon-ion laser 60 delivers UV light through a shutter 62 into a quartz optical fiber coupled to a microlens located in one instrument channel of the colonoscope, while the white light 64 is delivered through shutter 66 the illumination fibers of port 70. The pair of shutters 62, 55 are computer-controlled by a digital input/output (I/O) card 74. Both the fluorescence and white light images are detected by the CCD 72 at the distal end. A frame grabber 78 digitizes the fluorescence and white light images sequentially. A host microcomputer executes the image processing algorithm and displays the pseudo-color overlay. A mavigraph is used to convert the white light image with overlay into a format which can be recorded by the VCR.

Figure 6:
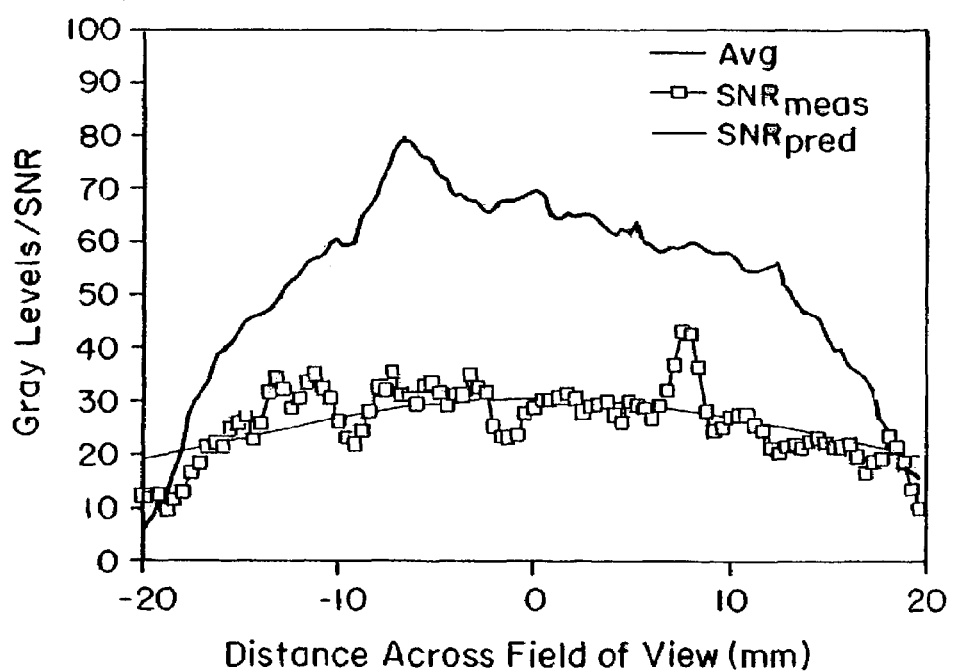
FIG. 6 is a graphical illustration of the average fluorescence intensity and the measured and predicted signal to noise (SNR) ratio.

The plot in FIG. 6 shows the fluorescence intensity from the average of 14 frames collected with the electronic imaging system. A row of pixels is shown from normal colonic mucosa. Also plotted are the measured and the predicted SNR. The SNR is approximately 30 at the center and it falls to about 10 near the periphery. Thus, the full field of view satisfies the minimum SNR requirement of 4 for the instrument-noise limited detection for distinguishing between normal colonic mucosa and adenomas.

Figure 7A:
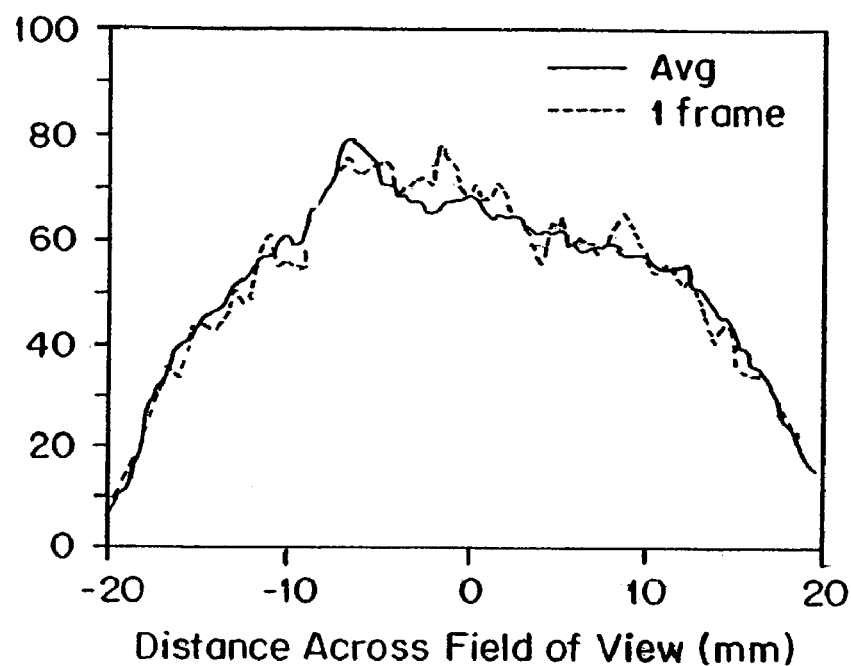
FIGS. 7A and 7B are graphical illustrations of variation fluorescence intensity between an average of 14 frames and a single frame for normal colonic mucosa and adenoma, respectively.
Figure 7B:
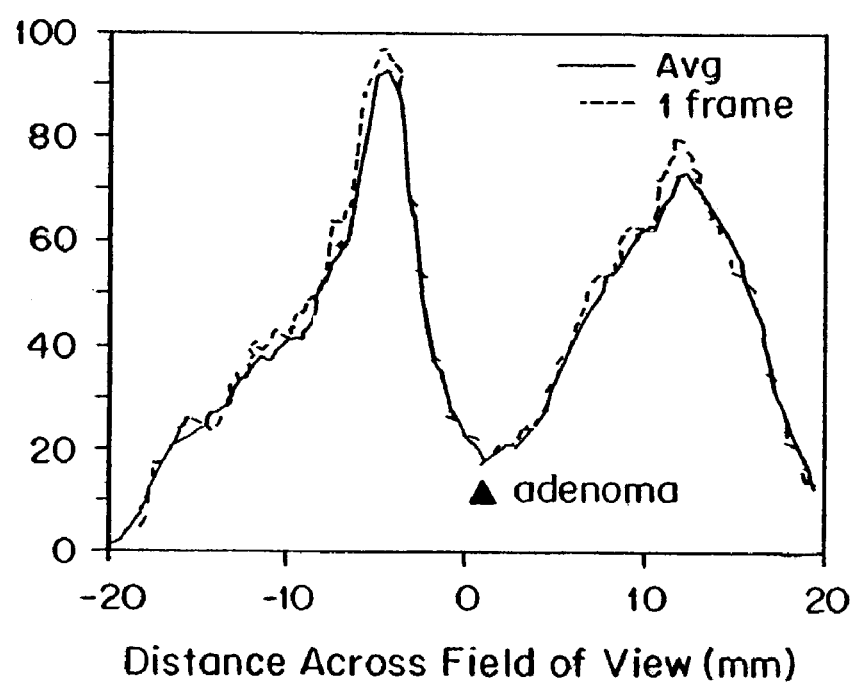

A frame-to-frame variation from average in the fluorescence image intensities can be seen in FIGS. 7A and 7B, which show the differences between the values across a row of pixels in a single frame compared to the average of 14 frames. The plot in FIG. 7A is that for the normal specimen shown in FIG. 6, and the plot in FIG. 7B is from a sample of mucosa which contains an adenoma in the center. The variation about the average is small compared to the difference in fluorescence intensity between normal and adenomatous tissue. Thus, the occurrence of false positives resulting from pixel-to-pixel variation is small.

A streaking artifact appeared in the fluorescence images taken with the electronic imaging system. This artifact arose because the UV excitation light was not blocked with the CCD rows were being read out electronically, which is performed under normal white light illumination by a rotating wheel with spatially separated filter. This artifact can be removed in the processing software of the image data.

A study was performed to determine the level of UV light which can be safely delivered onto the colonic mucosa. White light and fluorescence images were collected sequentially. Fluorescence images from 30 patients with 14 colonic adenomas and 6 hyperplastic polyps were collected. Finally, the fluorescence images were collected in parallel with single point EEM spectra. From these studies, the effectiveness of the real-time implementation of fluorescence image collection, processing, and display with movement in the colon were assessed. In addition, sources of artifact present on the colonic mucosa such as mucous, stool, and prep were evaluated. Also, the anatomy of the colon makes it desirable to collect images at large incident angles, and the effectiveness of the moving average algorithm with these limitations were determined. Finally, the intensities from fluorescence images were compared to that from the single point optical fiber probes.

The excitation source used was a Coherent Innova 328. This laser is rated for 1 W in the UV, and requires 60 A at 208 V of electrical power and 3 gal/min of water. The excitation light is coupled into an optical fiber device including lengths of 12.5 and 16.5 m of fiber were required to deliver the excitation light to the distal end of the colonoscope.

First, the excitation fiber must be incorporated in the colonoscope. Next, a method is used to rapidly switch between white light and laser illumination. Finally, a method of quickly and accurately registering the fluorescence results with the white light images must be implemented.

The colonoscopy procedures included prep of the patient with 3 oz of Fleet phospha soda mixed with 4 oz of water. There was no measurable fluorescence from the prep mixture using an optical fiber contact probe on the colonic mucosa in vitro with 370 nm excitation.

Figure 4:
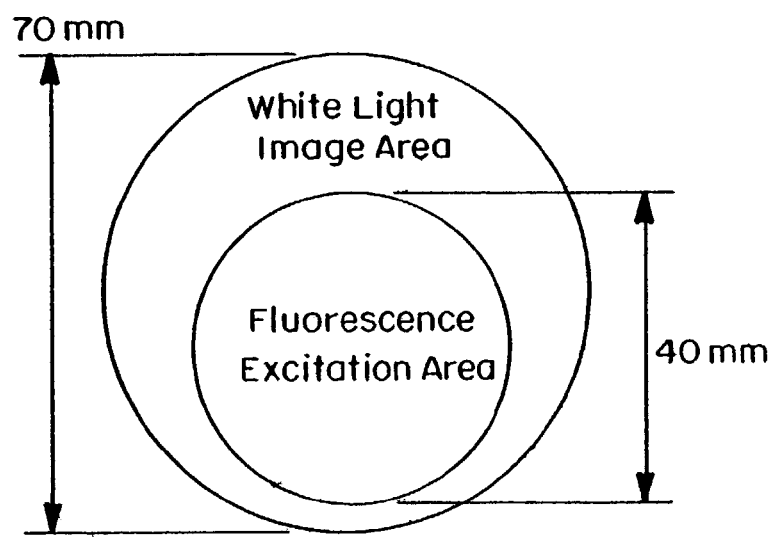
FIG. 4 shows the relative sizes of the illumination area and fluorescence area.

Using the electronic endoscope, white light reflectance and fluorescence images were collected sequentially in vivo during routine colonoscopy. The white light image can include a vascular pattern of arteries in red, and an outline of a vein in blue. Patches of specular reflection can be seen on the lower half of the images. The fluorescence of normal mucosa appears uniform with an arterial pattern interspersed as reduced fluorescence intensity. This effect is attributed to the absorption of fluorescence emission by hemoglobin. The vein does not appear on the fluorescence image, and there is virtually no specular reflection from the excitation light. The illumination filed on fluorescence is slightly smaller than that on white light, as depicted in FIG. 4.

An example illustrates the process of image collection, processing and evaluation of adenomatous polyps. A white light endoscopic image taken of a sporadic polyp located in the rectum shows a polyp with visible architectural features about 5 mm in diameter is located in the lower half of the image near the middle. In the raw fluorescence image the adenoma appears as a region of reduced intensity surrounding a brighter central region.

This image was ratioed with its own moving average image, and multiplied by 100 to produce the percent ratio image. Thresholds on the processed fluorescence images taken at 60%, 75%, and 90% were used to determine the contour lines which define regions of mucosa with various likelihoods of containing dysplasia. The contours were then filled in pseudocolor to highlight areas of tissue to be targeted for biopsy. The pseudocolors red, green and blue designate regions on the white light image which have high, medium and low probability, respectively. The polyp was found to be adenomatous on histology.

Overlay regions indicating disease included one located at the site of the adenoma, and the other two corresponded to shadows cast by mucosal folds. The shadows appeared as regions of reduced intensity on the fluorescence image. These effects were minimized by directing the endoscope normal to the mucosal surface. Moreover, the overlay regions which resulted from shadows changed in size and shape as the angle of the endoscope to the tissue surface varied, while those generated from the adenoma remained fixed in size.

White light and fluorescence images were collected from a total of 30 patients undergoing routine colonoscopy, which included images from 14 adenomas and 5 hyperplastic polyps. A biopsy was taken of each adenoma and one adjacent normal site. The fluorescence images were processed by the moving average algorithm, and the sensitivity of detection was determined as a function of threshold values ranging from 55% to 90%. The results of sensitivity are plotted in FIG. 8.

Figure 8:
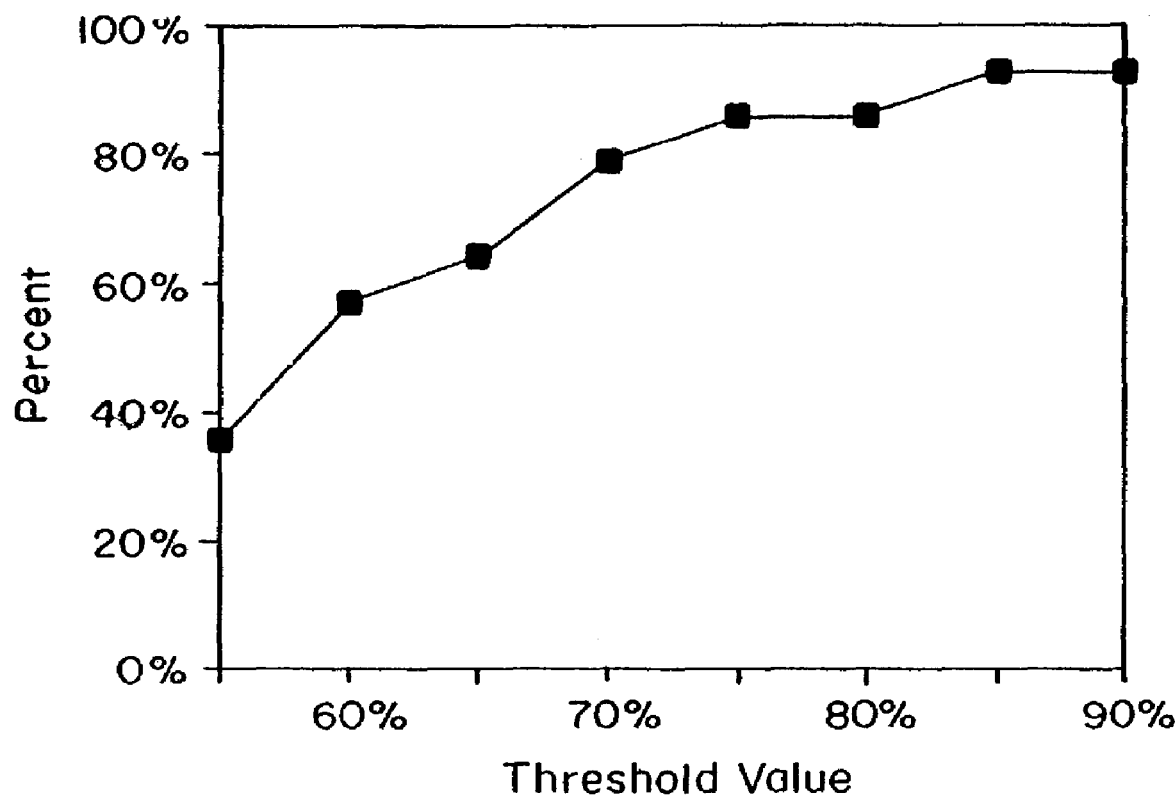
FIG. 8 is an illustration of the sensitivity of the system as a function of detection threshold values.

Autofluorescence images of colonic mucosa can be collected endoscopically in vivo and can be used to identify and localize dysplasia in the form of adenomatous polyps. The SNR of the fluorescence images was typically above 30. The adenomas were correctly identified by the fluorescence algorithm with high sensitivity. As shown in FIG. 8, the sensitivity of in vivo detection when the images are collected at normal incidence is comparable to that from the in vitro studies. At a threshold of 75%, the sensitivity for detection of colonic adenomas was 86%, compared to that of 92% for the in vitro experiments. In order to determine the specificity, the true negatives and false positives must be identified. However, true negatives (false positives) correspond to regions of normal mucosa which were found to be normal (diseased) on fluorescence. These results were not obtained because additional biopsies incur additional risk of perforation. Furthermore, the fluorescence from hyperplastic polyps, which are not dysplastic, did not result in regions of disease from the moving average algorithm.

In comparison of image size, the in vivo images encompassed regions of mucosa as large as 10×10 $cm^2$, whereas the specimens of colonic mucosa were only 2×2 $cm^2$ in the in vitro study. In such large fields of view, the colon contains many mucosal folds, and these layers of tissue blocked the excitation light from reaching the posteriorly-located normal mucosa, thus creating shadows. These folds were not present in the in vitro studies. Diagnostic errors on the processed fluorescence image resulted primarily from these shadows. The fluorescence method used is based upon the difference in intensity between normal and dysplastic mucosa. However, shadows appear as regions of reduced intensity without dysplasia being present. This artifact can be explained by the fluorescence excitation geometry. The fluorescence excitation is provided by one fiber located in the biopsy port for convenience. The center of this instrument channel is 8.3 mm away from the center of the CCD detector. The white light image, on the other hand, is illuminated by two fibers whose centers are located only 3.8 mm from the detector. Thus, the shadows on the white light image are much less pronounced than those on fluorescence.

The fluorescence technique used a single fluorescence emission band for detection of adenomas. This method worked well in vitro when the colonoscope is placed at normal incidence to the lesion, and no mucosal folds were present. However, during the clinical use of the fluorescence prototype, the view of the endoscope was often limited to the side of the adenoma. Because the colon is a tube-shaped structure, some adenomas were anatomically located at sites where it was virtually impossible to orient the colonoscopy at normal incidence to the lesion. As a result, one side of the lesion may not be surrounded by normal colonic mucosa. Another situation was that the normal mucosa is far away to produce fluorescence intensities sufficiently higher than that of the adenoma.

Figure 9:
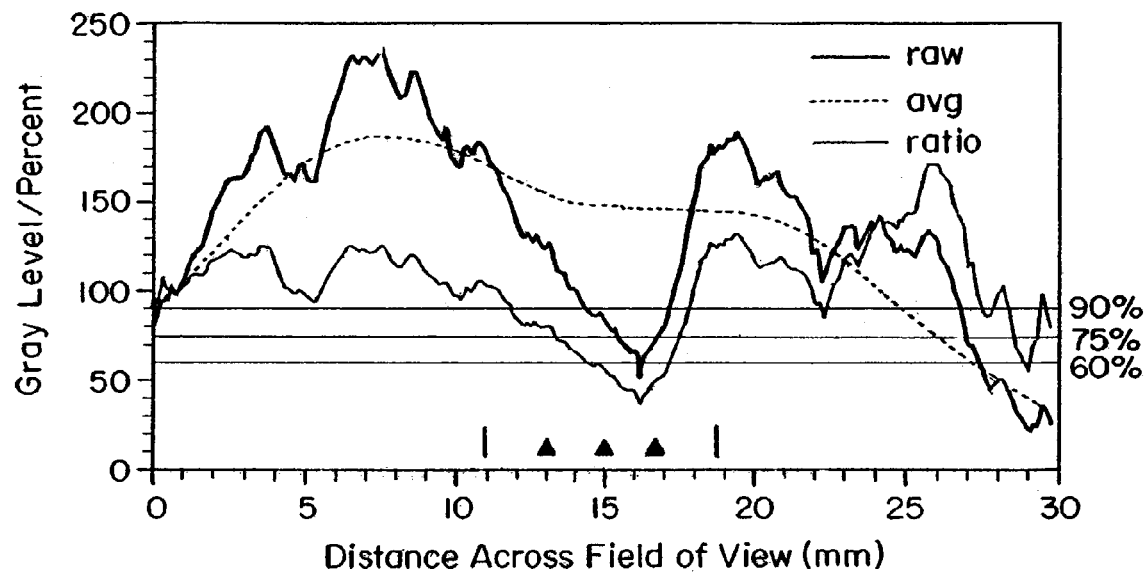
FIGS. 9 and 10 show fluorescence intensity profiles of tissue with adenoma, and including the moving average and percent ratio values.

The fluorescence intensities were measured from the raw images. The normalized intensity values and the intensity ratios were taken at three sites within the adenoma (denoted by left, center, and right in Table 3). The plot in FIG. 9 contains fluorescence intensity profiles through the adenoma, representing the raw fluorescence and percent ratio values, respectively. The adenoma was approximately 8 mm in diameter. On fluorescence, the lesion is located between the 11 mm and the 19 mm markings on the abscissa, which are labeled by the vertical lines near the x-axis in FIG. 9. Most of the adenomas exhibited a single fluorescence intensity minimum at the center of the lesion; the average ratio between normal and diseased pixels was 1.8±0.5 at the center, and 2.0±0.6 and 2.0±0.7 at the left and right midpoints, respectively. The average intensity ratio at these sites was 2.0±0.6. The results of this procedure show that the differences between normal colonic mucosa and adenomas for in vivo fluorescence images are very similar to that in vitro.

Figure 10:
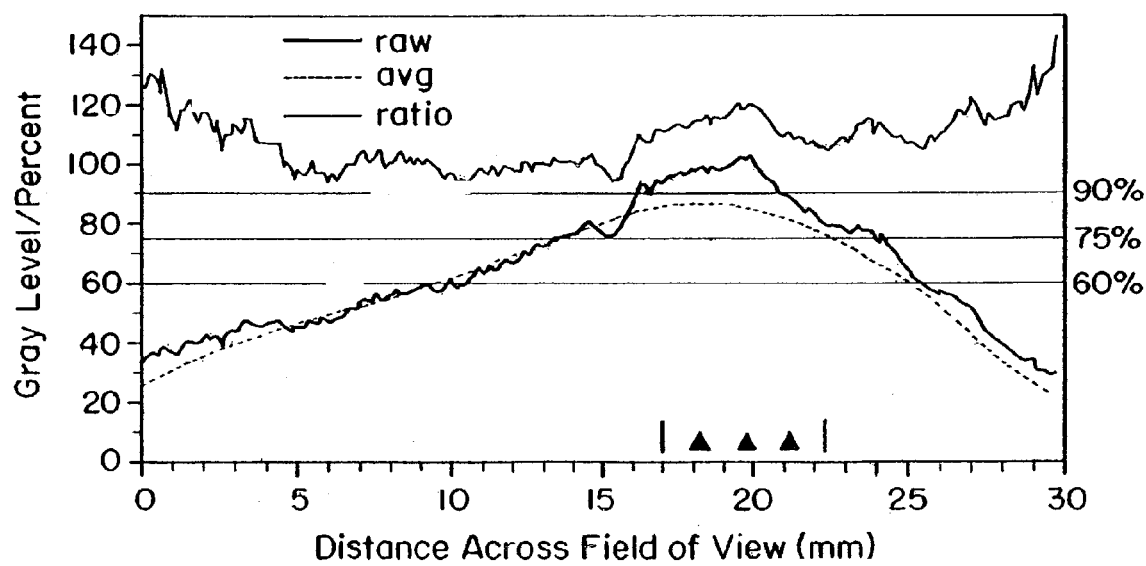

Similarly, the fluorescence intensities were measured from the raw images for hyperplastic polyps. The normalized intensity values and the intensity ratios were taken at three sites within the polyp (denoted by left, center, and right in Table 3). The plot in FIG. 10 shows the fluorescence intensity profiles through the hyperplastic polyp, representing the raw fluorescence and percent ratio values, respectively. The hyperplastic polyp was approximately 5 mm in diameter. On fluorescence, the lesion is located between the 17 mm and the 22 mm markings on the abscissa, which are labeled by the vertical lines near the x-axis in FIG. 10. The hyperplastic polyps exhibited an approximately uniform fluorescence intensity across the lesion which was continuous with the normal colonic mucosa. The average ratio between normal and diseased pilxes was 1.1±0.1 at the center, and 1.2±0.1 and 1.1±0.2 at the left and right midpoints, respectively. The average intensity ratio at these sites was 1.1±0.2. Because this average ratio value is not significantly different from that of normal mucosa, it is not surprising that no region of disease could be identified by this intensity method.

In the in vivo images, the vascular pattern was clearly displayed on both the white light and fluorescence images. The vessels were not apparent on the in vitro images, perhaps because the blood supply of the living colon was no longer intact. The hemoglobin in the blood is a well-known absorber of light, and produces linear patterns of weak fluorescence intensity. Thus, the intensities were measured from the raw fluorescence images of blood vessels. As shown in Table 3, the intensity ratio from the blood vessels is 1.3±0.1. This value is significantly less than the average from adenomas, thus blood vessels will not present as a source of artifact on the overlay. Furthermore, image processing methods can be used to remove the blood vessels based on their shape. In Table 3, the intensity ratios for adenomas, hyperplastic polyps, and blood vessels are summarized for comparison.

Endoscopic images and single point spectra can both provide valuable information about tissue biochemistry. Each method has its own advantages and disadvantages. The endoscope collects images, and provides spatial information with sub-millimeter resolution. The fluorescence intensity between normal mucosa and adenomas can be compared from the same image field within a fraction of a mm from each other. Also, fluorescence images are collected remotely, thus the pressure on the tissue is uniform throughout the image field. However, it is more difficult to acquire spectral information with fluorescence. Because of the larger areas involved, the fluorescence energy may become too weak at each pixel to maintain sufficient SNR, unless very large excitation power is used.

On the other hand, single point optical fiber contact probes collect fluorescence from an area of approximately 1 mm in diameter only. With an intensified optical multi-channel analyzer (OMA), spectra over a wide bandwidth can be measured with a good spectral resolution and high SNR. However, the probe must be placed at several sites on the mucosa to sample differences between normal and adenoma. Typically, the normal mucosa sampled is several cm away from the adenoma, and comparisons of the absolute intensity can be affected by biological variability over distance.

The degree of contact of the probe on the polyp can vary during the in vivo measurements because the colonic musculature is constantly contracting and expanding. As a result, movement is created which makes probe placement difficult. The adenoma is round and slippery, and the movement of the colonic wall renders complete contact with the surface of the polyp very difficult. Furthermore, the distal end of the optical fiber probe is not flat, but there is a 17° bevel. Thus, the orientation of the beveled side will affect the degree of contact as well.

Results of the colonoscopy procedure showed that it was very difficult to place the probe onto the polyp for the 0.5 seconds required to collect a full EEM. Light escaping at various colors representing the excitation sources was observed on the normal mucosa surrounding the adenoma. This observation suggests that the delivery of excitation energy to the polyp and collection of fluorescence emission was not complete. Probe contact was hindered by the physiological movement of the mucosa, and by the fact that a flat probe was being placed on a slippery, hemispherical surface. Contact is not a problem for spectra collected on normal mucosa because this surface is flat.

Figure 11:
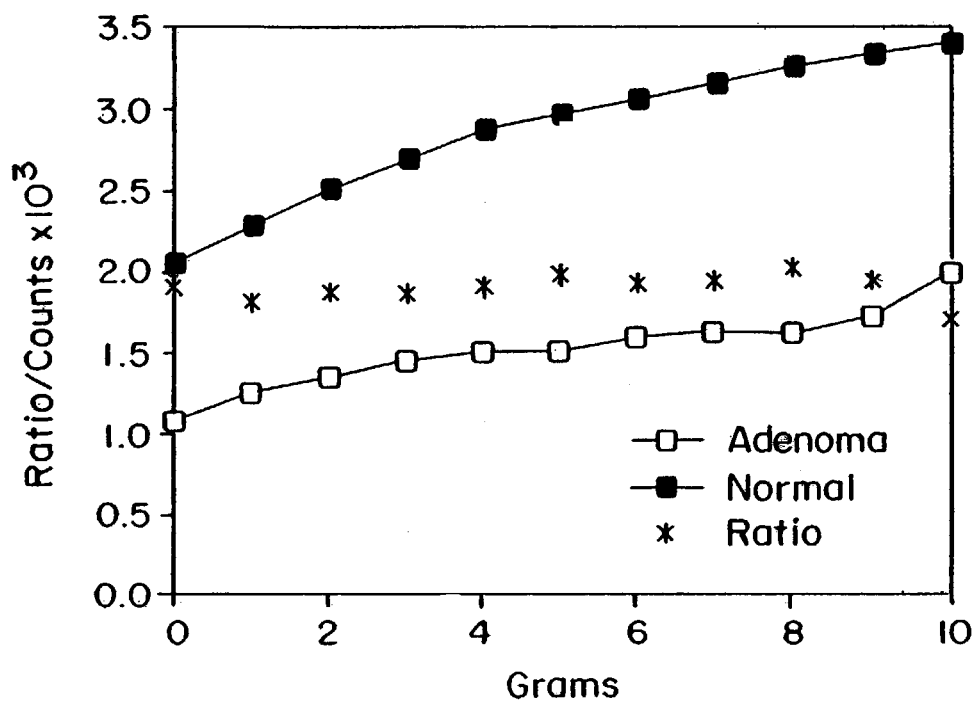
FIG. 11 is the fluorescence intensity graph showing adenoma, normal and intensity ratio values as a function of pressure exerted on the site with the probe.

Moreover, the ratios between the intensities of normal mucosa and adenomas can be affected by difference in the pressure exerted on each site. An in vitro experiment was conducted on a resected specimen of colonic mucosa which contained an adenoma. The fluorescence intensity in the spectral range between 400 and 700 nm was measured as a function of pressure exerted by the probe which was passed through the biopsy channel of a colonoscope. The pressure was measured with a balance. As shown in FIG. 11, the fluorescence intensity increased with pressure, and the intensity ratio does not change if equal pressure is exerted on both the normal and ademona sites. However, this is usually not the case during the clinical acquisition of spectra. The normal mucosa is relatively flat, and measurements can be made with virtually complete probe contact with a few grams of pressure. On the other hand, the pressure on the polyp cannot be made the same as that on the normal site because the probe will slip off. The pressure on the normal site was estimated to be about 5 grams, while that on the adenoma was estimated to be close to zero. Thus, the difference in pressure exerted on the normal mucosa and the adenoma may result in the intensity ratio increasing from 2 to 3, as shown in FIG. 11.

Furthermore, on the recorded images of the colonoscopy procedures, the normal mucosa showed an indentation at the site where the probe was placed during the collection of spectra. This observation confirmed the estimate that several grams pressure was exerted on normal mucosa during data collection. On the other hand, the probe was seen to slide off the polyp when any significant pressure was exerted, which resulted from the moistness of the surface. Thus, the pressure exerted on adenomas was significantly less.

Another procedure was conducted in vitro to compare the fluorescence intensity ratio between normal mucosa and adenoma as measured on imaging and single point. White light and fluorescence images of a resected specimen of colonic mucosa containing two adenomas were obtained. The intensities were measured for 7 normal sites immediately adjacent to the adenomas on both imaging and single point. The results included the intensities that were normalized so that the average value is 100 for each system. This step allows for direct comparisons to be made at each point, and reveals that the intensities are within about 10% of each other. Furthermore, the normalized intensity values range from 68 to 155 on imaging and from 63 to 136 on single point. Thus, the intensities-measured on normal mucosa depend on the site sampled with both methods, and can vary by over a factor of 2.

In Table 4, the normalized intensities and the intensity ratios are determined for the two adenomas on imaging and single point. These values are determined at the center and the left and right midpoints of the adenomas. For the left adenoma, the average intensity ratio was 1.43 on imaging and 1.54 on single point. For the right adenoma, the average intensity ratio was 1.52 on imaging and 1.72 on single point. These results indicate there is little difference in the intensity ratios between imaging and single point in vitro.

Figure 12:
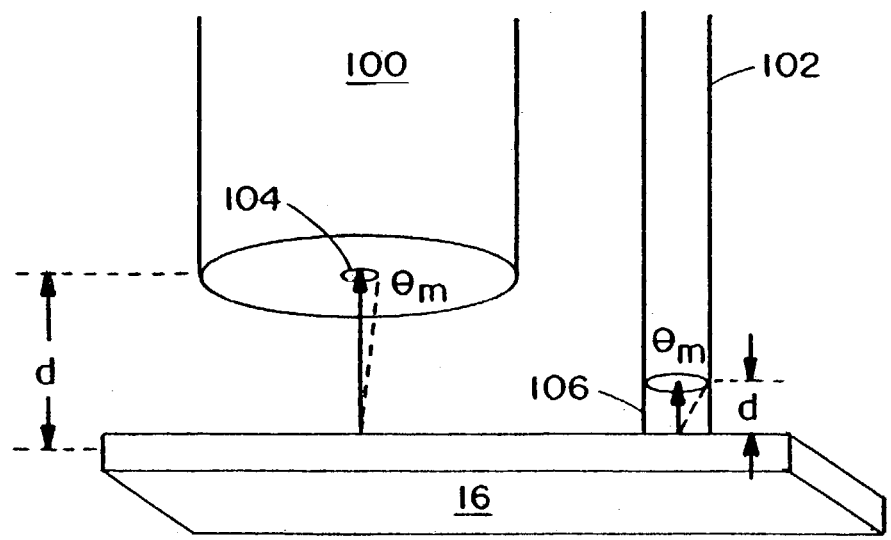
FIG. 12 is an endoscope system showing the difference in collection geometry between the endoscope and a contact probe.

The fluorescence intensity ratio was calculated from Monte-Carlo simulations to determine the fluorescence intensity ratio, given the different excitation and collection geometries of the imaging system and single point. In FIG. 12, a diagram of the collection geometry for the endoscope 100 and the single point probe 102 is shown. The endoscope contains a 2.5 mm diameter objective lens 104, and is located in air at a distance 20 from the surface of the tissue. This geometry corresponds to a collection angle of 40°. The probe contains a quartz shield 106 which is in contact with the tissue 16. The optical fibers are located at a distance of 2 mm from the tissue surface by this shield 106, and collect light at a NA=0.22, which corresponds to a collection angle of 12.7°. The optical parameters of colonic mucosa for the excitation and emission wavelengths are shown in Table 2.

The excitation used in the simulation is an infinitely-thin beam with a divergence angle of 0°. The fluorescence intensity at a point on the tissue from a uniform thick excitation beam can be determined from the fluorescence collected from a superposition of infinitely-thin excitation beams which are incrementally displaced in distance from the point to be measured. However, this result is equivalent to integrating the fluorescence intensity over the field of view. The LSF of the tissue falls off quickly within several mm, thus the simulation integrates over a 2 mm region within the collection angle specified in Table 5. The results of the simulation are shown in terms of the intensity ratio between the light collected at the tissue surface with that of the excitation. In Table 5, the intensity ratio between normal colonic mucosa and adenomas is 3.0 and 2.9 for the endoscope and the probe, respectively. The intensity ratio is similar for the endoscope and the probe, a result which is consistent with the in vitro studies. The intensity ratio for the endoscope is slightly higher than that of the probe, which is consistent with the collection angle of the endoscope being smaller. Light from the highly fluorescent submucosa is more likely to reach the detector with a smaller collection angle.

A model was developed to quantify the number of photons collected by the endoscopic imaging system over the field of view at normal angle of incidence. This result is valid for both white light reflectance and fluorescence images, and can be applied to both the fiber optic imaging bundles and electronic imaging systems. The spatial distribution of the illumination and emission profiles of in the center and to fall off towards the periphery of the image. When combined with the detector noise statistics, the SNR of the image can also be determined. This analysis showed that distance and optical collection geometry produces a profile in which the SNR at the periphery was always lower than that in the center. This parameter is needed for developing algorithms for identifying tissue lesions. Also, the collected light intensity was found to decrease with the square of the distance between the distal end of the endoscope and the tissue. Furthermore, the light collection by coherent imaging bundles is limited by the numerical aperture of the optical fiber. This analytic tool can be used to design the optical parameters of the fluorescence imaging system and to identify the type of light source required to excite the fluorescence.

The methods developed for endoscopic imaging model were used to determine the excitation source, optics, and detectors necessary for building two fluorescence imaging systems. The first design consisted of a fiber optic colonoscope which detected the fluorescence image at the proximal end with an intensified CID camera. A 400 nm long pass filter was used to block the reflected excitation light, and a quartz optical fiber located external to the colonoscope was used for image excitation. The second design was a modification of the first to accommodate the requirements for clinical use. This system used an electronic colonoscope with dual instrument channels, and detected fluorescence images at the distal end. The cutoff in spectral sensitivity of the CCD detector below 400 nm was used to avoid the reflected excitation light. An illumination probe with a high NA quartz optical fiber was coupled to a microlens and inserted into one instrument channel for image excitation. In both systems, the excitation source was an argon-ion laser which delivered about 300 mW at $\lambda_{ex}$=351 and 364 nm, and microcomputer with a frame grabber was used to acquire, process, and display the diagnostic images.

Autofluorescence images from human colonic adenomas were collected with the fiber optic system with high SNR in vitro. For wide area surveillance of the colon wall, regions of mucosa as large as 100 mm$^2$ must be illuminated. Furthermore, the endoscopic images are collected remotely, and the intensity collected falls with distance d squared. Previously, fluorescence spectra were collected from contact probes which illuminated an area of about 1 mm$^2$. The results of this study showed that excitation sources, optics, and detectors used in this design could collect autofluorescence images with sufficient SNR to distinguish between normal colonic mucosa and adenomas. In the fiber optic system, an SNR of over 30 was attained, which exceeded the minimum SNR requirement of 7.

Fluorescence images were then collected from samples of resected colonic mucosa in vitro to evaluate the potential use of this technique for wide area surveillance of dysplasia Colectomy specimens from three patients with familial adenomatous polyposis containing polypoid and non-polypoid adenomas were studied. Each raw image was corrected for differences in distance and instrument light collection efficiency by normalizing to a spatially averaged image. Intensity thresholding was then used to identify diseased regions in mucosa. The sensitivity and specificity for detecting a region of dysplasia depended on the threshold value selected. With the threshold set to 75% of the average normal intensity, a sensitivity of 90% and a specificity of 92% were achieved. The average fluorescence intensity from normal mucosa was found to be greater than that from the adenomas by a factor of 2.2±0.6. These results demonstrate the potential of this technique to direct biopsy site selection.

The results from the in vitro studies provided motivation for conducting an in vivo study. The electronic system was used to collect autofluorescence images from colonic adenomas in vivo. In the this system, an SNR of over 30 was attained as well, which exceeded the minimum SNR requirement of 4. Fluorescence images were collected from 14 adenomas and 6 hyperplastic polyps from 30 patients undergoing routine colonoscopy. The fluorescence images were collected in a 33 ms frames, and were processed by dividing the raw fluorescence image with a moving average image. The processed images displayed regions of mucosa with a probability of containing dysplasia in the form of adenomas, as verified on histology. With the threshold set to 75% of the average normal intensity, a sensitivity of 86% was achieved for detecting adenomas and a specificity of 100% was attained for hyperplastics. On average, the ratio between the fluorescence intensity of normal mucosa to that from adenomas was 2.0±0.6 and to that from hyperplastic polyps was 1.1±0.2. The diseased regions on fluorescence best corresponded to the adenoma on white light when the colonoscope was at normal incidence. At higher angles there were greater effects from shadows. These results showed that dysplasia can be identified on fluorescence images in vivo.

In the single point optical fiber contact probe studies the average intensity ratio between the fluorescence at 460 nm from normal colonic mucosa and adenomas was found to be about 3, while that in endoscopic imaging this ratio was measured to be 2.0+0.6. Direct comparison of fluorescence imaging and single point measurements in vitro revealed that there was little difference between the intensity ratio measured on imaging compared to that measured from single point. There are two possibilities that can account for the difference in intensity ratio between the two methods. First, the ratio of 3 measured by the single point method was performed in vivo. A lower ratio may have resulted in vitro because of the loss of blood flow, which is known to absorb light.

Alternatively, the difference in the ratios may result from contact and pressure artifacts. Videotapes of the colonoscopy procedure showed that it was very difficult to place the probe onto the polyp for the 0.5 seconds required to collect a full EEM. Light at various colors representing the excitation sources was observed, which indicated that the delivery of excitation energy to the polyp and collection of fluorescence emission was not complete. Probe contact was hindered by the physiological movement of the mucosa, and by the fact that a flat probe was being placed on a slippery, hemispherical surface. Contact is not a problem for spectra collected on normal mucosa because this surface is flat. Furthermore, increased pressure was found to elevate the fluorescence intensity collected. Higher pressures were exerted on the normal mucosa compared to that on the polyp. The probe was seen to slide off the polyp when any significant pressure was exerted. Both differences in contact and pressure in vivo resulted in a higher ratio between normal mucosa and adenoma. On the other hand, the fluorescence images are collected remotely, and the pressure and contact parameters are identical for normal mucosa and adenoma.

Finally, the results of the clinical studies identified future directions to improve the sensitivity and clinical usefulness of fluorescence endoscopic imaging. The shadow artifact can be reduced by illuminating the tissue through the two white light ports. This modification can be accomplished by replacing the glass fibers with quartz, thus allowing for both white and excitation light to be transmitted. Furthermore, the shadow artifact, angle of incidence, and detection yield can all be improved by collecting multi-spectral images consisting of two or more fluorescence images. Lastly, the concurrent collection of EEM spectra can be used to identify new excitation wavelengths which result in higher intensity contrast ratios.

Dysplastic tissue exhibits an increase in red fluorescence which can be detected to improve the sensitivity of disease detection. Thus another embodiment includes the collection of multiple emission wavelengths. One method of collecting multiple fluorescence emission wavelengths is to use an electronic endoscope (e.g. Olympus, Model CF I OOTL) with a CCD detector which is sensitive to the red, green, and blue (RGB) regions of the visible spectrum. Fluorescence images from each RGB frame can be captured and processed, providing more detailed information for use in a diagnostic procedure. Furthermore, the use of spectral line-shape information from images at different wavelengths reduces all geometric distortions. The TI TC244 has a quantum efficiency of 30% at 640 nm and 15% at 480 nm [TI Mannual, 1994]. Extrapolating from the 370 nm imaging data and the EEM data, the SNR of 10:1 in the red and 50:1 in the blue is anticipated.

Performing the detection on the distal end of the electronic colonscope has many practical advantages. First, the same detector can be used for both white light and fluorescence imaging. A single detector not only results in a perfect registration of the two images, but avoids the need to interchange of cameras, which can be cumbersome. Second, fewer optical elements results in a transmission efficiency of fluorescence photons which is significantly higher than that of a fiber optic imaging bundle. Third, the packing geometry of CCD pixels allow for minimal loss of surface area of detection, unlike fiber optic imaging bundles which have a hexagonal packing array.

While there are advantages to detecting the fluorescence image with a distally located CCD, a fiber optic imaging bundle with proximal detection has advantages as well. The spectral bands of the distal CCD is limited to the RGB response of the distal detector, while the fluorescence collected by a fiber optic imaging bundle could be filtered into an unlimited number of spectral images. Also, detection of the fluorescence image at the proximal can allow for detection with a gated intensifier. This device enables use of pulsed lasers.

The EEM study provides valuable guidance about new imaging strategies. The results indicate that excitation near 410 nm is useful. The contrast between normal and adenoma tissues provided by the blue fluorescence is greatly enhanced compared to that obtained with our current excitation wavelength (10:1 versus 2:1). In addition, the red fluorescence is quite pronounced for adenoma. Extrapolation of the conclusions of the morphological model developed using $\lambda_{ex}$=365 nm to this new excitation wavelength suggests that the blue fluorescence contains information about both crowding of the crypts and mucosal thickness, and that the red fluorescence contains information about crypt cell dysplasia. Hence, collecting images at red and blue emission wavelengths should provide both high contrast diagnostic images and significant new histological information. In addition, the ratio image can be used to normalize out shadow effects. The next phase of the imaging studies will use 410 nm excitation. A krypton ion laser (Coherent Innova Model 302) will provide 500 mW of power at the two lines 407 and 413 nm. This level of power is adequate to achieve large fluorescence signals in both red and blue bands. This laser will be installed at the BWH Laser Laboratory along with the existing 365 nm argon ion laser.

In addition, multiple excitation wavelengths can be employed. One approach would be to use excitation from the 407 and 413 nm lines of a krypton ion laser to excite the red fluorescence and to retain the 365 and 351 run lines from argon ion laser to excite the blue fluorescence. Two hardware configurations include (1) a fiber endoscope with a switchable filter wheel between the scope and camera, and (2) a dual-chip endoscope. Such a system has been developed, for example, by American Hospital, Inc., for stereo viewing during endoscopy. One can modify one of the windows on the chip with a spectral cut-off mechanism. The timing of the red-sensitive imaging channel can be synchronized with the excitation light.

The diffuse reflectance image at 407-413 nm can be explored to obtain information about the tissue hemoglobin content. This image can be obtained by installing a filter with the appropriate bandwidth on the rotating wheel in front of the white light source. The approach is to ratio this reflectance image with the fluorescence images in the red and blue frames. In order to develop the required algorithms, and to decide how to optimize the spectral information collected, an extensive contact probe study with 410 nm excitation can be performed.

The shadow artifact obtained using the broadband intensity algorithm with 365 nm excitation can be greatly reduced by use of an improved excitation geometry. Currently, excitation light is delivered through a single quartz fiber located in the biopsy channel located 8.3 mm from the CCD detector. The use of a single illumination beam located a large distance from the CCD chip tends to enhance shadows. In contrast, in the conventional while light images produced by this colonoscope, shadows are minimized by use of two closely spaced white light illumination beams symmetrically positioned on opposite sides of the CCD chip. By replacing the illumination fibers with quartz fibers, the UV light can be delivered through the two white light illumination ports, which are located only 3.8 mm from the CCD detector. Implementing this requires modifying the video processor to enable alternate coupling of white light and laser excitation into the illumination fibers.

Other spectral endoscope improvements can include: (i) regulating the excitation light intensity on the tissue surface via feedback control. This provides constant illumination, regardless of viewing distance, and is also important for patient safety; (ii) minimizing the streaking effect of the fluorescence excitation on the white light endoscopic imaging display by timing the fluorescence excitation to occur during the "blank" periods of the filter wheel used in the endoscope white-light source. Feedback control of the excitation light can be accomplished by measurement of the average intensity on the fluorescence image. The intensity of this average value will be used to modulate the open period on the shutter or filter wheel. The streaking effect can be completely removed by implementing the identical filter wheel for blocking the excitation light that is used for producing the RGB illumination on the white light mode.

As described above, a large argon-ion laser was used as a near-LTV excitation source for imaging studies. Although adequate for these studies, this light source is expensive and bulky and operates at only a few discrete wavelengths. Such a laser system with its special electrical and water cooling requirements cannot be easily moved, preventing use at multiple sites. Alternative excitation sources can be considered which include a pulsed laser and a white-light source with filters, both of which are compact and transportable.

For applications in which near-UV excitation is appropriate, a pulsed ND:YAG laser is used because it can provide third harmonic radiation at 355 mm with sufficient average power for spectral imaging. In both the in vitro and in vivo studies, good SNR was obtained with 300 mW of laser power, which corresponds to 10 mJ of energy per frame. Therefore, a frequency tripled ND:YAG laser with a 5-10 ns pulse duration operating at 30 Hz with an average power of 300 mW at 355 nm will be adequate. Using a CCD camera gated at about 10 ns, this short excitation pulse enables simultaneous acquisition of white light and fluorescence images. Within this short temporal gate the white light background is negligible, obviating the need to chop the white light illumination. There are no special power or water requirements for lasers of this type and a fluorescence endoscope system with such a laser will be easily transportable.

A mercury lamp can also be used as an excitation source. Such a source is compact and lightweight and can provide a bright, narrowband illumination at a number of excitation wavelengths. Employing this light source simplifies system design and reduce cost, enabling less expensive units to be produced for use at multiple sites. The key issue is whether enough light in the desired wavelength range can be coupled into the illumination fiber(s). A commercial white light source with a 150 W xenon lamp is capable of delivering as much as 80 mW of white light at the distal end. Utilizing a 50 run excitation bandwidth, about 20 mW of light can be used to induce tissue fluorescence.

At selected wavelengths, mercury lamps have 5 to 10 times higher output powers than that of xenon. This indicates that with a 500 W mercury lamp having a relatively small filament, at least 300 mW of useful excitation light should be available at the distal end of the illumination fibery should be sufficient for collection of good quality fluorescence images from colonic tissue. In addition, to further enhance SNR, either the total area of illumination can be reduced or imaging elements can be binned together.

A lamp and power supply can be selected for this application with the proper brightness, stability and minimum electrical interference.

Currently, the image processing scheme is based on ratioing the raw image to a spatially-averaged image, and applying a threshold criterion for classifying a region of tissue as normal or diseased. The averaging window and detection threshold values are pre-flexed, regardless of the polyp size, viewing angle and distance. The predetermined values limit the range of polyp sizes which can be accurately measured. Improved image processing and thresholding methods will employ variable window sizes for spatial averaging and variable thresholds. Information from the raw digitized image about the diameter of the largest lesion in the image will be used to determine these parameters. This change in the window size as a function of the lesion in the image field will maximize the intensity ratio and optimize the performance of the fluorescence method.

Image analysis methods for extracting information from multivariate images can also be explored. A multivariate image is a collection of congruent images of the same object measured with different variables, such as reflected wavelengths, or fluorescence or Rainan band intensities. Many methods are available for analyzing multivariate images, and they can be adapted to image analysis. In general, three steps will be followed, image processing, object segmentation, and contrast measurement. The images will first be processed based on the selected operation, such as moving-window average, intensity difference or ratio. The processed image will then be segmented based on both frequency and intensity information. This can be done either through thresholding, quick/slow descent, or region growth. These methods can be coupled to the concomitant identification and display of a lesion(s) based on a probabilistic scheme.

When techniques for collecting multiple spectral images are developed and a database of such images are built, more advanced image analysis methods, such as principal component analysis and regression analysis can be used. Principal component analysis does not assume a known (a priori) distribution, but instead employs a set of calibrated data to extract information about structures exhibiting pre-malignant changes. The regression technique is based on the principle of building up a mathematical relationship between two groups of variables, i.e., between a number of independent variables and one or more dependent variables. As an example, a logistic regression to correlate spectral intensities in the images with histopathology of dysplastic lesions.

The development of the fluorescence imaging endoscope has demonstrated the potential to perform wide-area surveillance colonscopy using fluorescence. The fluorescence image can be analyzed in real time and can provide the endoscopist with an instant interpretation of the probability of dysplasia determined using a previously-validated algorithm. In addition, the ability to guide biopsy can be used with the present invention. In patients with FAP, fluorescence imaging can be used to direct mucosal biopsies to areas that are endoscopically normal-appearing (non-polypoid) but, based on their spectral characteristics, can have an increased likelihood of being dysplastic. Histopathological assessment of mucosal biopsies will be correlated with spectral data to validate for detection of "flat" dysplasia.

The following method can be followed for determining the capability of the fluorescence imaging system for directing biopsy. The entire surface of the colon wall, both at colonscopy and using resected samples at colectomy, is systematically imaged, and isolated areas which are diagnosed as dysplastic selected for directed biopsy. Random areas diagnosed as benign can also be sampled and the spectral diagnosis confirmed by histological analysis. Again, the effects of complications such as inflammation can be investigated. Once an imaging algorithm has been validated, it can be adapted to the detection of dysplasia in patients with UC. As in the case of the contact probe studies, diagnostic algorithms for UC must be capable of evaluating patients with various degrees of background inflammation. The same patient groups studied with contact probe EEMs will be studied with fluorescence imaging. An important potential benefit of wide area fluorescence surveillance is that one or more of the otherwise random biopsies obtained during conventional surveillance colonscopy may be directed by the results of fluorescence imaging. Those biopsies can be separated from the remainder of the random biopsies to assess whether fluorescence imaging can increase the yield of dysplasia detection over random sampling.

The development of the rapid EEM and spectral imaging systems represent two very important advances in instrumentation. Two systems are complementary. The imaging system views wide areas of mucosa in real time, and the EEM system provides complete spectral characterization of a given site of colonic mucosa. The two instruments can be used simultaneously, where appropriate. The EEM probe is placed through the second channel of a two channel colonscope. Thus, each system can be used to verify the other. Also incorporated herein is the publication attached hereto and entitled "Real-Time in vivo endoscope imaging of fluorescence from human colonid adenomas."

The following table compares the signal size expected for white light imaging, fluorescence imaging observed with the endoscope CCD, and the fluorescence imaging using the optics module with the intensified CID camera. The parameters listed below are taken from either the manufacturer's specifications or from experimental measurements.

TABLE 1

| Imaging Device | Definition | Pentax (white light) | Pentax (fluorescence) | UV Module |
|---|---|---|---|---|
| $\lambda_{ex}$ (nm) | ex wavelength | | 356 | 356 |
| $\lambda_{em}$ (nm) | ex wavelength | | 460 | 460 |
| $\Delta\lambda$ (nm) | em bandwidth | 400–700 | 400–700 | 400–700 |
| $P_o$ (mW) | power | 1 | 300 | 300 |
| $\Delta t$ (s) | integration time | 0.011 | 0.011 | 0.033 |
| d (mm) | distance | 20 | 20 | 20 |
| Diameter (mm) | area illum | 70 | 70 | 28 |
| $\theta_m$ (degrees) | max angle | 60 | 60 | 35 |
| $N_f$ (pixels/fibers) | number | 88560 | 88560 | 10000 |

TABLE 1-continued

| Imaging Device | Definition | Pentax (white light) | Pentax (fluorescence) | UV Module |
|---|---|---|---|---|
| $r_L$ lens (mm) | radius | 1.25 | 1.25 | 0.3 |
| $\epsilon_t$ | tissue efficiency | 1 | 5.00E−05 | 5.00E−05 |
| $f_o$ | packing fraction | 1 | 1 | 0.6 |
| $T_f$ | % trans filter | 1 | 1 | 0.8 |
| $T_i$ | % trans imaging | 1 | 1 | 0.9 |
| $T_o$ | % trans optics | 1 | 1 | 0.9 |
| $\eta_s$ | photocathode eff. | 0.2 | 0.2 | 0.1 |
| g | group factor | 1 | 1 | 1 |
| $N_s$ | signal photons | $1.7 \times 10^5$ | 2500 | 338 |
| $\sigma_e$ | electronic noise | 55 | 55 | 50 |
| G | gain | 1 | 1 | 10,000 |
| SNR | signal/noise | 407 | 34 | 18 |

TABLE 2

| | normal | | adenoma | |
|---|---|---|---|---|
| $\lambda$ (nm) | $\lambda_{ex} = 370$ | $\lambda_{em} = 460$ | $\lambda_{ex} = 370$ | $\lambda_{em} = 460$ |
| $\mu_a$ | 0.9 | 0.45 | 2.1 | 1.1 |
| $\mu_s$ | 15.0 | 9.5 | 8.5 | 5.9 |
| g | 0.9 | 0.9 | 0.9 | 0.9 |
| mucosal thickness (μm) | 450 | 450 | 1000 | 1000 |
| quantum eff (mucosa) | 0.1 | 0.1 | 0.8 | 0.8 |
| quantum eff (submucosa) | 0.1 | 0.1 | 0.8 | 0.8 |

TABLE 3

| | Adenoma | Hyperplastic | Blood Vessels |
|---|---|---|---|
| | Normalized Intensity | | |
| Normal | 100.0 ± 27.5 | 100.0 ± 18.1 | 100.0 ± 16.1 |
| Left | 54.0 ± 16.3 | 87.9 ± 16.3 | |
| Center | 59.9 ± 16.7 | 95.9 ± 16.7 | 75.3 ± 5.1 |
| Right | 54.4 ± 17.7 | 98.1 ± 17.7 | |
| | Intensity Ratio (normal/lesion) | | |
| Average | 2.0 ± 0.6 | 1.1 ± 0.2 | 1.3 ± 0.1 |
| Left | 2.0 ± 0.6 | 1.2 ± 0.1 | |
| Center | 1.8 ± 0.5 | 1.1 ± 0.1 | |
| Right | 2.0 ± 0.7 | 1.1 ± 0.2 | |

TABLE 4

| | Imaging | | Single Point | |
|---|---|---|---|---|
| | Normalized Intensity | Intensity Ratio | Normalized Intensity | Intensity Ratio |
| Left Adenoma | | | | |
| Left | 65 | 1.54 | 58 | 1.72 |
| Center | 74 | 1.35 | 74 | 1.35 |
| Right | 71 | 1.41 | 65 | 1.54 |
| Avg. | 70 | 1.43 | 66 | 1.54 |
| Right Adenoma | | | | |
| Left | 61 | 1.64 | 57 | 1.75 |
| Center | 81 | 1.23 | 67 | 1.49 |
| Right | 59 | 1.69 | 52 | 1.92 |
| Avg. | 67 | 1.52 | 59 | 1.72 |

TABLE 5

| | endoscope | | probe | |
|---|---|---|---|---|
| | normal | adenoma | normal | adenoma |
| d (mm) | 20 | 20 | 2 | 2 |
| $\theta_m$ (deg) | 4 | 4 | 12.7 | 12.7 |
| $n_o$ | 1.0 | 1.0 | 1.4 | 1.4 |
| $n_t$ | 1.4 | 1.4 | 1.4 | 1.4 |
| 370 | 2.8E−02 | 2.8E−02 | 4.2E−03 | 6.2E−04 |
| 460 | 8.8E−05 | 2.9E−05 | 2.8E−03 | 9.7E−04 |
| Ratio | 3.0 | | 2.9 | |

Figure 13:
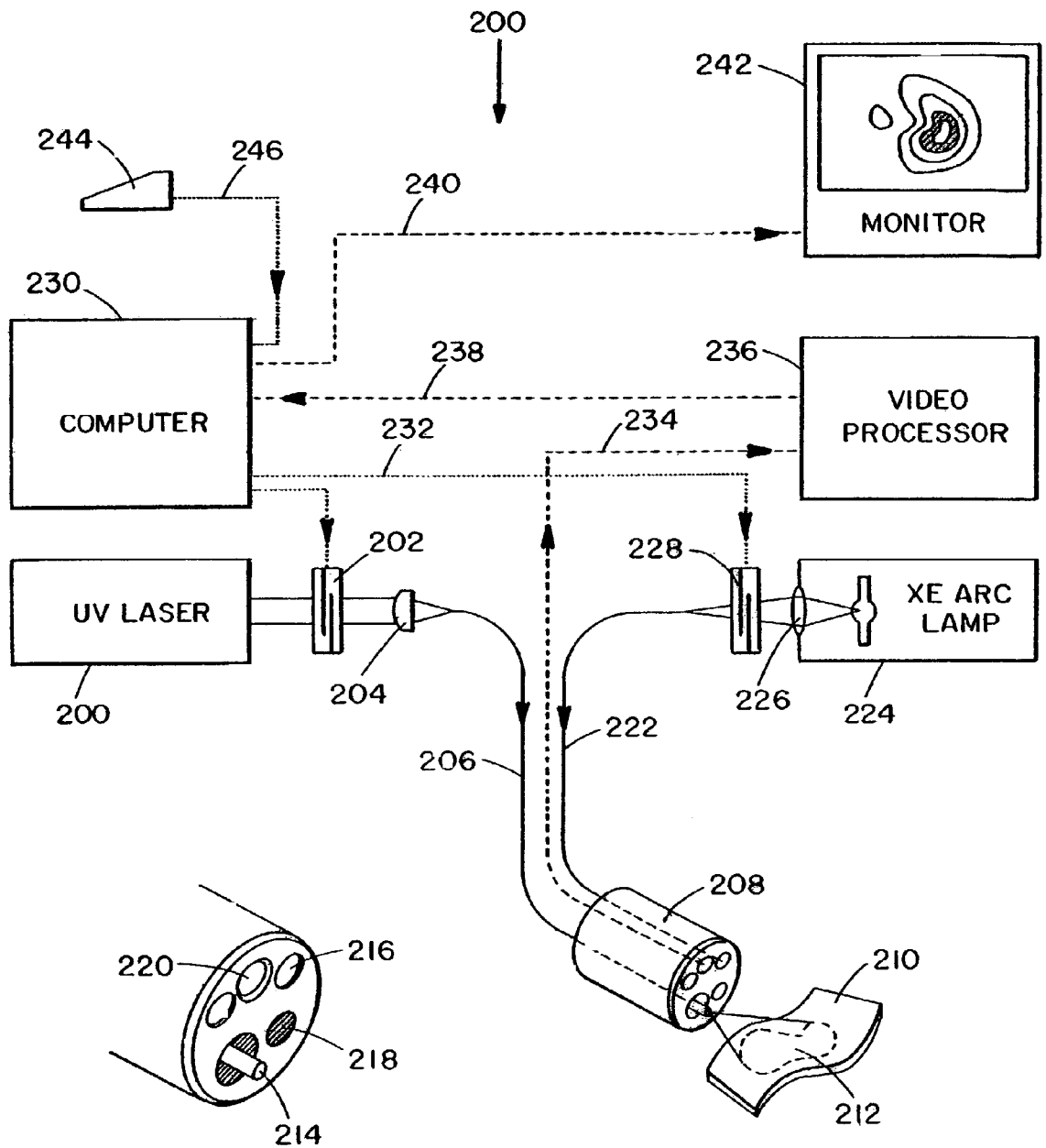
FIG. 13 is a preferred embodiment of an endoscope system in accordance with the invention.

FIG. 13 presents a schematic outline of the system which has been demonstrated in clinical practice in a format which will allow comparison with the improved systems to be described below. The embodiment shown uses an ultraviolet laser source 200, switched by a shutter 202 and focused with a lens 204 into a fused silica fiber probe 206 inserted into a biopsy channel of an endoscope 208 to deliver it to a tissue site 210 so that it can illuminate the tissue over an area 212. The UV illumination thus comes from an aperture 214 which is different from the endoscope's own illumination ports 216. In the dual-channel Pentax endoscopes used in the clinic this procedure leaves one biopsy channel 218 free.

The endoscope camera 220 obtains its white light illumination through its own fiberoptic illuminator 222 from a broadband Xenon arc lamp 224 and collection optics 226. A non-standard shutter 228 under computer 230 control 232 is attached to allow the white light illumination to be turned off while fluorescence images are being taken. The fluorescence image signal 234 is processed by the endoscope's video processor 236 to produce a standard video signal 238 which is digitized by a framegrabber in computer 230. The processed image signal 240 with its information on the state of the observed tissue is sent to monitor 242. The entire diagnostic procedure is initiated by a foot switch 244 attached to the computer by a cable 246.

Figure 14A:
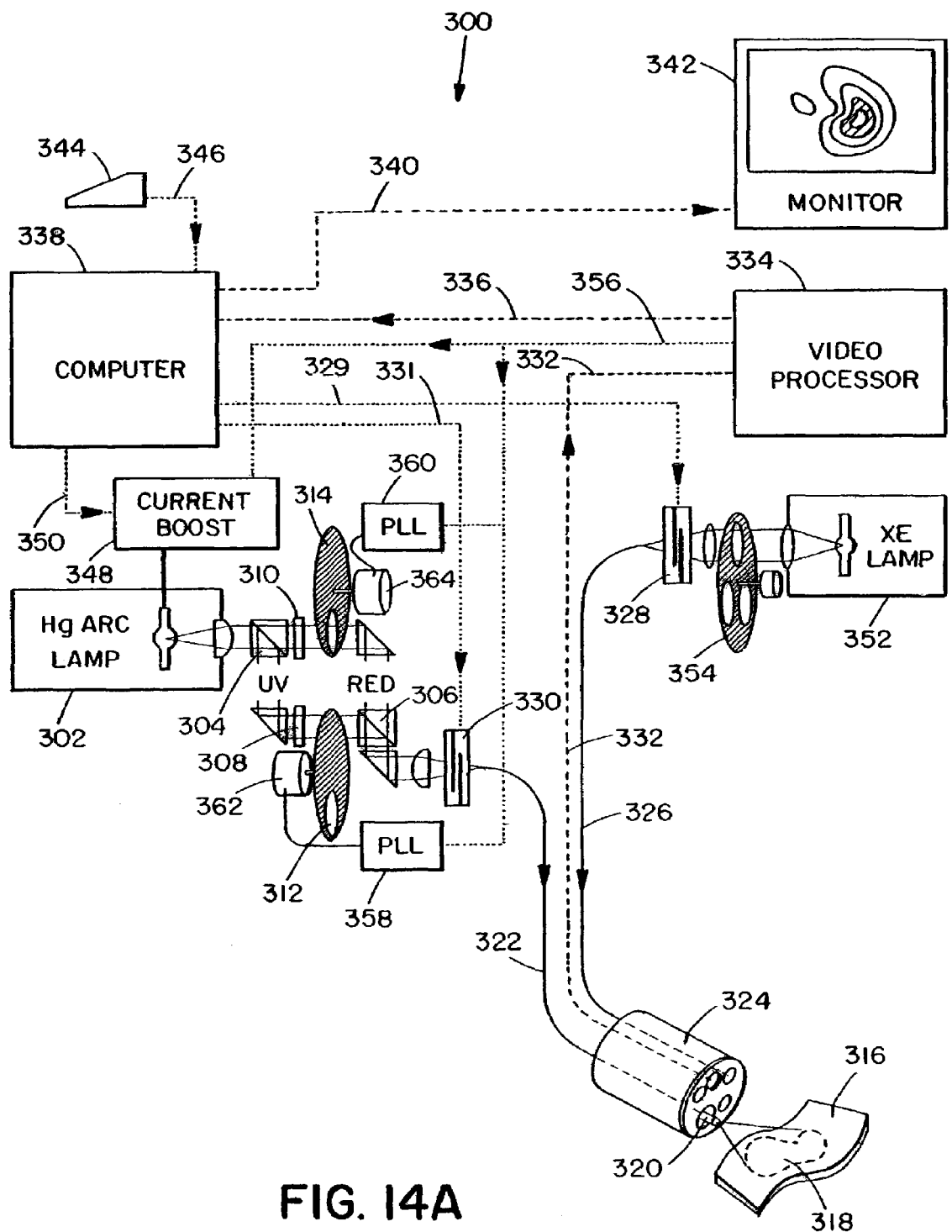
FIG. 14A is a preferred embodiment of a fluorescence imaging system in accordance with the invention.

FIG. 14A shows a design for the fluorescence imaging system which eliminates the tendency of the previous system to identify shadows in the image as regions of dysplasia. The improved design uses a 100 W mercury (Hg) arc lamp light source 302, dichroic mirrors 304 and 306, wavelength filters 308 and 310 and rotating shutters 312 and 314 to provide precisely-timed, tissue-illumination pulses in two separate wavelength bands. The first wavelength band is centered on the near-ultraviolet (365 nm) mercury resonance line and is used to obtain the UV autofluorescence image. The second wavelength band is at the end of the visible spectrum and is used to obtain a simultaneous or near-simultaneous, reflectance image for the purpose of identifying shadows and the extent of the UV illumination field.

A reflectance (non-fluorescing) image taken with an endoscope camera system measures the brightness of the tissue surface 316 in its field of view. To the extent of the tissue surface is a Lambertian (non-specular) reflector (generally the case) this image indicates the distance of the tissue from a single illumination source (or a weighted distance from multiple sources). If these illumination sources are not in the direct line-of-sight from the camera to the tissue source there will be shadows. A reflectance image can thus be used to measure both the UV illumination 318 at the tissue surface and the presence of shadows in the fluorescence image as long as the UV illumination and the visible illumination emanate from the same aperture 320 with the same angular divergence. Note that this condition can be satisfied either by a two-color illumination fiber 322 passed through a biopsy channel of an endoscope 324 or by the two-color illumination being passed through the illumination bundle 326 of the endoscope. A shutter 328 switches off the normal white-light illumination of the endoscope while the two diagnostic images are being obtained. The closing of shutter 328 under computer control 329 occurs at the same time as the opening of shutter 330 by control line 331. This action enables the two-color light to reach the fiber 322 and thus the tissue 316.

The algorithm for using the visible reference image along with the fluorescence image is as follows. The video signals 332 from the CCD camera at the distal tip of the endoscope 324 are converted by the video processor 334 to a standard NTSC color video signal 336 and sent to a video framegrabber in computer 338. The two images are first corrected for the gamma factor applied to the video signal by the video processor to insure that the digitized images acquired by the framegrabber in the computer are linear measurements of the tissue surface brightness. This is accomplished in real time by the framegrabber input look-up table. The two images are then normalized to their peaks, which will generally be a region of non-dysplastic tissue in the visual field. This normalizes the two illumination fields. On a pixel-by-pixel basis the fluorescence image value is then divided by the visible reference image value. If the ratio falls below a predetermined threshold (typically on-half to one-third) then that pixel in the image represents a region of reduced fluorescence which is indicative of dysplasia. This pixel can then be set to a false color state in an output video signal 340 sent to a monitor 342 to indicate to the clinician the probability of dysplasia. A prior threshold requirement on both images insures that the ratio obtained is significant and eliminates false color output in regions of shadow of low illumination at the edges of the video field. This entire operation occurs for every depression of the footswitch 344 which is connected to the computer through cable 346.

In the improved design both the UV-excitation light pulse and the visible-reference light pulse are delivered to the tissue through the same optical fiber 322 inserted through a biopsy channel of the endoscope. The condition that the two illumination sources have the same angular distribution is assured by the design of the light collection apparatus shown in FIG. 14A. A single Hg arc lamp 302 is used as the source of both wavelengths. A dichroic mirror 304 reflects the UV portion of the spectrum and transmits the visible portion. Filters in each path further refine the bandwidth of the two beams. The UV filter 308 must reject visible light to a high degree since the efficiency of the 460 nm tissue fluorescence is only about 0.1%. The filter 310 in the red path is less critical but the chosen center wavelength should avoid hemoglobin absorption bands to provide the best reference image. Note that the design of the beam splitting optics and beam combining optics have an even number of reflections in both the UV and visible arms. This assures that any angular deviations of the output beams due to motion of the lamp track each other. It also makes the directions of the output beams invarient under translations and small rotations of the beam splitting and recombining optics as a whole.

Figure 14B:
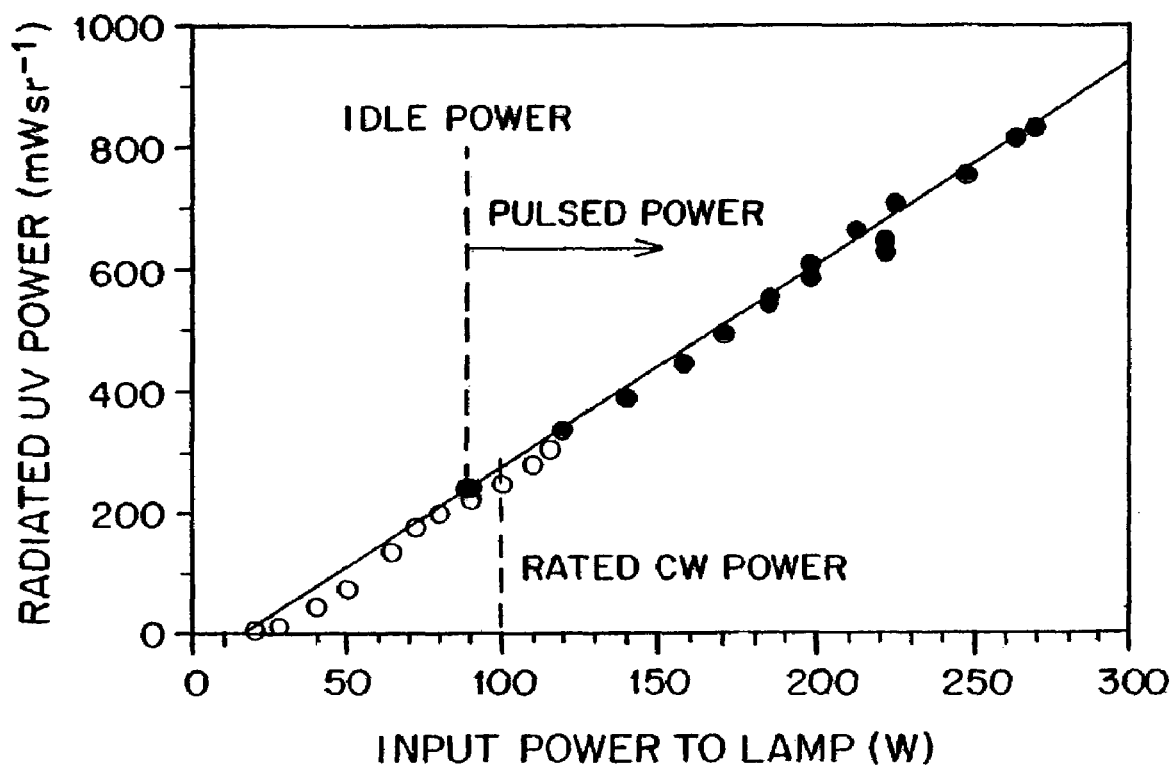
FIG. 14B illustrates graphically the dependence of radiated power on the input power of a light source emitting in the ultraviolet region of the spectrum.

In the improved source design the current through the Hg lamp 302 is boosted at appropriate moments to increase the lamp output power for the UV exposure. This allows a larger area of tissue to be scanned for dysplasia in a single image. The data in FIG. 14B show that the UV output power from a 100 W Hg lamp is a linear function of its input power to at least a factor of 3 over its nominal rated power. Since the lamp discharge maintains a constant voltage drop across the arc regardless of current, the lamp output power is essentially proportional to current. At least 50% power to the lamp must always be maintained, however, to keep the mercury in the vapor phase. The lamp power supply 348 in the improved fluorescence system utilizes a DC current section to maintain the idle current and a computer-controlled 350, pulsed current section which can rapidly switch in multiple constant-current sources to vary the output power of the lamp as required by the imaging system. If the idling power is kept below the rated power and the current pulses are kept to a sufficiently small duty factor, then the pulsed UV output can be sustained continuously.

Figure 14C:
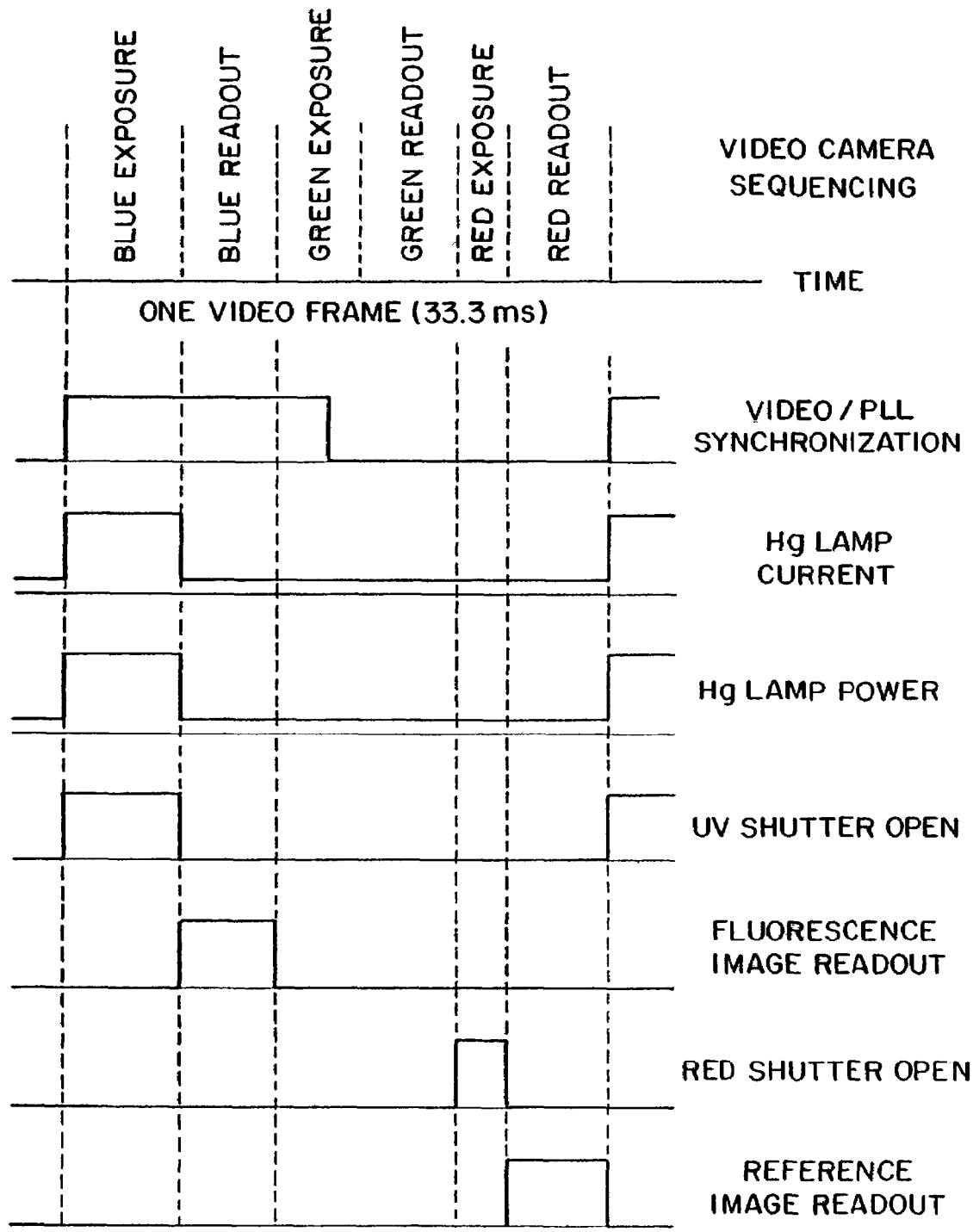
FIG. 14C illustrates a timing diagram for a process acquiring fluorescence and reference images.

The rotating shutter in the UV path 312 and in the red path 314 of the light source are designed to provide pulsed illumination light according to the timing diagram in FIG. 14C. This diagram shows how this fluorescence imaging system is used with a monochrome camera, which uses a xenon arc lamp 352 for illumination and a rotating blue-green-red filter wheel 354 to synthesize a color image from 3 monochrome images. In this type of system a pulse of blue light first illuminates the tissue for about 6 milliseconds and the resulting tissue reflectance image is digitized for the next 6 milliseconds. The illumination must be turned off during the readout period because the monochrome camera used continues to collect photo current in the pixels as they are line shifted to the readout electronics. Illumination during the readout causes a smearing artifact in the image. The UV illumination is switched in during the normal blue exposure period and the red light illumination is switched in during the red exposure period. The green exposure period is not generally used but could be used to obtain an additional reference image or an additional UV fluorescence image. The shutters are timed to the video acquisition system using an LM1881 Video Sync Separator circuit to develop and even/odd frame synchronization pulse 356 from the standard composite video output signal. Phase-locked-loops (PLL) and 358 and 360 synchronize the phase of the chopper wheels to this signal by varying a voltage to their DC driving motors 362 and 364. This signal is also used to synchronize the current pulser 348. In the schematic of FIG. 14A the chopper wheels are shown in collimated portions of the beam. In practice, these chopper wheels are placed at an internal focal point in the two arms of the optics train (not illustrated) to provide for fast rise and fall times for the light pulse.

Note that the dual-wavelength illumination method can also be used with standard, color-CCD camera endoscopes.

In this case, the UV light illumination and red light reference illumination are present simultaneously. The UV-induced fluorescence (primarily at 460 nm) is then detected by the blue-responsive pixels in the CCD camera and the reference reflectance image is detected by the red-responsive pixels. Note that the visible blue light must still be removed from the diagnostic illumination so as not to decrease the contrast of the fluorescence image. The slight amount of red tissue fluorescence seen in dysplastic tissue due to the UV excitation is much smaller than the level of direct red illumination. The slight increase also acts to reduce the fluorescence/reference ratio which properly increases (slightly) the measured probability of dysplasia.

Figure 15:
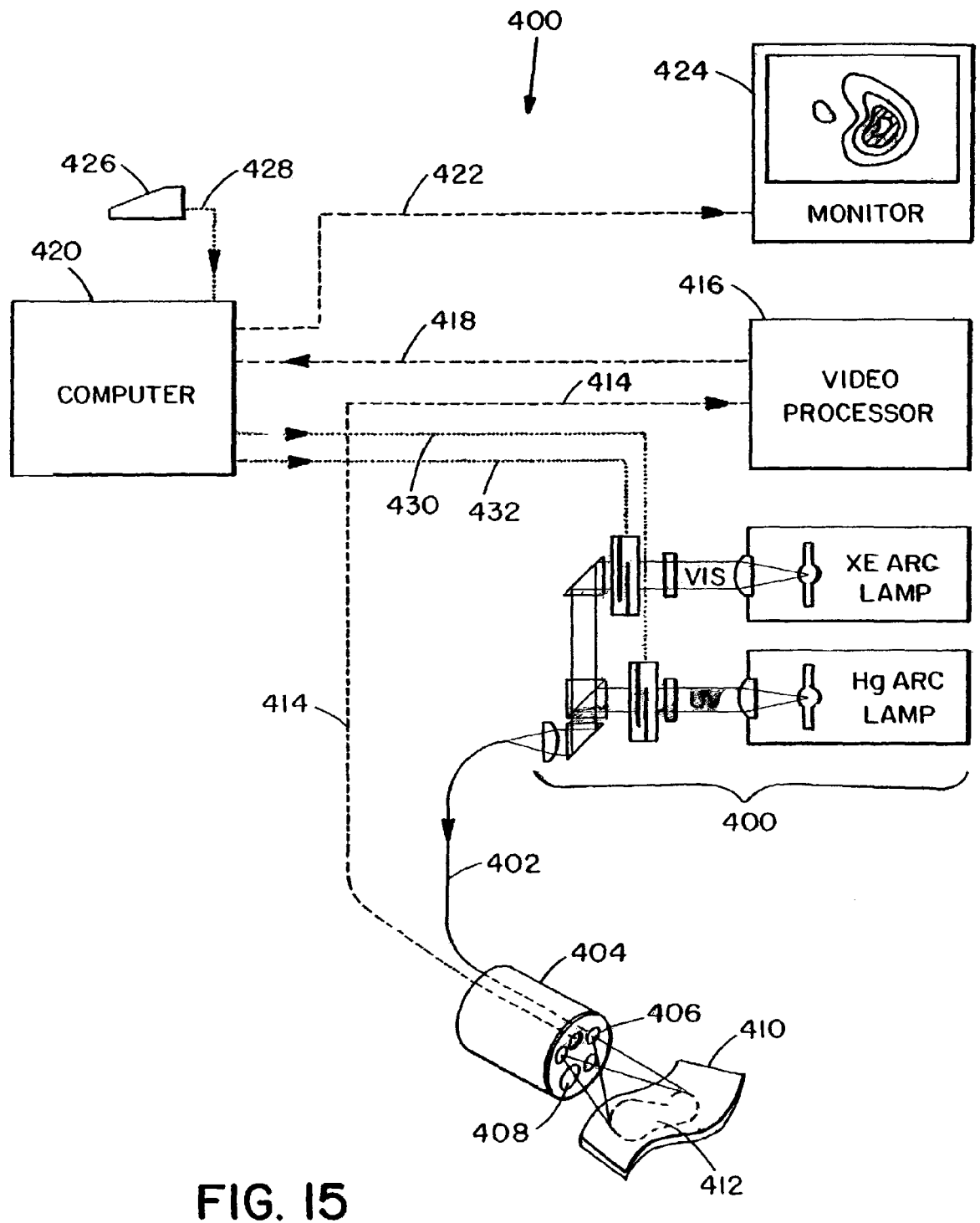
FIG. 15 is a preferred embodiment of a fluorescence imaging system in accordance with the invention.

FIG. 15 shows a preferred embodiment of the fluorescence imaging system in which dual wavelength illumination capability as well as white-light illumination capability is built into the video endoscope system itself 400. This requires the illumination bundle 402 of the endoscope 404 to be transmissive at UV wavelengths which is not usually the case with current commercial systems. Such a design fulfills the design requirement that the UV-excitation and visible-reference illumination emanate from the same aperture or apertures 406. Such a system would also be easier for an operator to use since the illumination fiber would not have to be threaded down through a biopsy channel 408 and those channels would be free for their standard uses. The tissue surface 410 would be illuminated over a larger area 412 with fewer shadows since dual illumination ports 406 are standard. The video signal 414 would be processed by the endoscope system 416, formatted into a standard signal 416 and processed by the computer 420. The output video signal with the false color overlay 422 would be sent to a monitor 424 for the clinician to see in real time. The diagnostic illumination would be initiated by a footswitch 426 connected by a cable 428 to the computer 420 with the light pulses controlled by signal lines 430 and 432 to the shutters in the light source.

While this invention has been particularly shown and described with references to preferred embodiments thereof, it will be understood by those skilled in the art that various changes in form and details may be made therein without departing from the spirit and scope of the invention as defined by the appended claims.

What is claimed:

1. A method of autofluorescence imaging comprising:
providing an endoscope having an optical guide that is optically coupled to a first broadband light source and a second laser light source that emits light at a wavelength in a range of 350 nm to 420 nm, the endoscope having an image sensor at a distal end;
collecting a reflectance image including red, green and blue components with the image sensor in response to illumination by said broadband light source;
collecting an autofluorescence image having a blue component, a green component and a red component with the image sensor; and
processing the autofluorescence image by determining a ratio of the autofluorescence image and the reflectance image to provide a processed fluorescence image.

2. The method of claim 1, further comprising providing an image sensor having a filter to remove ultraviolet light from light returning from tissue.

3. The method of claim 1, wherein the image sensor has a sensitivity in the ultraviolet region that is less than half of the sensitivity of the sensor in a visible region.

4. The method of claim 1, wherein the processing step corrects intensity for shadows in the autofluorescence image.

5. The method of claim 1, wherein the autofluorescence image is non-intensified.

6. The method of claim 1, wherein the broadband source comprises an arc lamp.

7. The method of claim 1 further comprising electronically switching between the first light source and the second light source.

8. The method of claim 1, further comprising compensating for shadows on a tissue surface to be imaged.

9. The method of claim 1, wherein the first and second light source are optically coupled to the same optical guide.

10. The method of claim 1, further comprising providing a shutter coupling each light source to an optical fiber.

11. The method of claim 1, further comprising imaging dysplasia on a tissue surface.

12. The method of claim 1, wherein the image sensor comprises a color-sensitive image sensor.

13. The method of claim 12, wherein the image sensor comprises a color charge coupled device (CCD).

14. The method of claim 1, wherein the image sensor detects red, green and blue wavelengths at separate exposure intervals.

15. The method of claim 1, wherein the image sensor comprises a pixellated flat panel detector.

16. The method of claim 1, wherein the step of collecting a autofluorescence image comprises collecting at least three wavelengths in a range of 400-700 nm.

17. A fluorescence imaging system comprising:
an endoscope;
a light source emitting at a wavelength in a range of 350 nm to 420 nm coupled to an optical guide extending through the endoscope;
a second broadband light source coupled to an optical guide extending through the endoscope;
an imaging sensor at a distal end of the endoscope that detects a fluorescence image having a blue component, a green component and a red component and reflectance image of tissue; and
a processor that determines a ratio of the fluorescence image and the reflectance image to provide a processed image.

18. The fluorescence imaging system of claim 17, wherein the light source comprises a narrow band light source.

19. The fluorescence imaging system of claim 18, wherein the narrow band light source comprises a laser.

20. The fluorescence imaging system of claim 17, further comprising a fiber optic device optically coupled to the light source.

21. The fluorescence imaging system of claim 17, further comprising a processor that compares image data with a threshold.

22. The fluorescence imaging system of claim 17, further comprising a shutter positioned along an optical path between the light source and an optical fiber extending through the endoscope.

23. The fluorescence imaging system of claim 17 wherein the image sensor has reduced sensitivity in an ultraviolet spectral region relative to sensitivity in a visible spectral region.

24. The fluorescence imaging system of claim 17, wherein the image sensor comprises a filter reducing image sensor sensitivity below 400 nm.

25. The fluorescence imaging system of claim 23, wherein the sensor sensitivity in the ultraviolet spectral region is less than one half of the sensitivity in the visible region.

26. The fluorescence imaging system of claim 17, wherein the imaging sensor comprises a color-sensitive image sensor.

27. The fluorescence imaging system of claim 26, wherein the imaging sensor comprises a color charge coupled device (CCD).

28. The fluorescence imaging system of claim 17, wherein the imaging sensor detects red, green and blue wavelengths at separate exposure intervals.

29. The fluorescence imaging system of claim 17, wherein the light source comprises a laser light source.

30. The fluorescence imaging system of claim 17, further comprising a processor that processes said fluorescence image and said reflectance image to produce a processed output image.

31. The fluorescence imaging system of claim 17, further comprising collecting three wavelengths in a range of 400-700 nm.

32. The fluorescence imaging system of claim 17, wherein the imaging sensor comprises a pixellated flat panel detector.

* * * * *